(12) United States Patent
Fesenko et al.

(10) Patent No.: US 11,156,623 B2
(45) Date of Patent: Oct. 26, 2021

(54) METHODS OF MONITORING SAFETY OF QUERCETIN COMPOSITIONS

(71) Applicant: PUBLIC JOINT STOCK COMPANY "SCIENTIFIC INDUSTRIAL CENTRE BORSHCHAHIVSKIY CHEMICAL-PHARMACEUTICAL PLANT", Kiev (UA)

(72) Inventors: Sergii Fesenko, Kiev (UA); Alexander Shneider, Dedham, MA (US); Vladimir Gabai, Brighton, MA (US)

(73) Assignee: PUBLIC JOINT STOCK COMPANY "SCIENTIFIC INDUSTRIAL CENTRE BORSHCHAHIVSKIY CHEMICAL-PHARMACEUTICAL PLANT", Kiev (UA)

( * ) Notice: Subject to any disclaimer, the term of this patent is extended or adjusted under 35 U.S.C. 154(b) by 351 days.

(21) Appl. No.: 16/226,795

(22) Filed: Dec. 20, 2018

(65) Prior Publication Data

US 2020/0200776 A1 Jun. 25, 2020

(51) Int. Cl.
*G01N 33/94* (2006.01)
*G01N 30/02* (2006.01)
(Continued)

(52) U.S. Cl.
CPC ........... *G01N 33/94* (2013.01); *A61K 31/353* (2013.01); *A61K 47/10* (2013.01); *A61K 47/12* (2013.01); *A61K 47/46* (2013.01); *G01N 30/02* (2013.01)

(58) Field of Classification Search
CPC ....... G01N 33/94; G01N 30/02; A61K 31/353; A61K 47/10; A61K 47/12; A61K 47/46
See application file for complete search history.

(56) References Cited

U.S. PATENT DOCUMENTS 7,745,486 B2 6/2010 Lines
8,044,096 B2 10/2011 Lines
(Continued)

FOREIGN PATENT DOCUMENTS

EA 201201593 A1 6/2014
WO WO-93/20168 A1 10/1993
WO WO-2016/007114 A1 1/2016

OTHER PUBLICATIONS

Anter, J. et al. (Mar. 1, 2011). "Antigenotoxicity, Cytotoxicity, and Apoptosis Induction by Apigenin, Bisabolol, and Protocatechuic Acid," Journal of Medicinal Food 14(3):276-283.
(Continued)

*Primary Examiner* — Brian J. Sines
(74) *Attorney, Agent, or Firm* — Mintz, Levin, Cohn, Ferris, Glovsky and Popeo, P.C.

(57) ABSTRACT

Provided herein are methods to determine the safety of quercetin compositions regarding contaminants that can result from the degradation of quercetin, such as by storage of solid form quercetin compositions in an air atmosphere. The contaminants include protocatechuic acid, 2,4,6-trihydroxybenzoic acid, and 2-(3,4-dihydroxybenzoyloxy)-4,6-dihydroxybenzoic acid. Provided herein are also methods which reduce degradation of solid form quercetin compositions and reduce the formation of such toxic compounds. The provided methods increase the shelf life and patient safety of quercetin compositions.

19 Claims, 20 Drawing Sheets

(51) Int. Cl.
  *A61K 31/353* (2006.01)
  *A61K 47/10* (2017.01)
  *A61K 47/12* (2006.01)
  *A61K 47/46* (2006.01)

(56) References Cited

U.S. PATENT DOCUMENTS

| | | | |
|---|---|---|---|
| 8,440,704 | B2 | 5/2013 | Lines |
| 2009/0186937 | A1 | 7/2009 | Lines |
| 2020/0197355 | A1 | 6/2020 | Fesenko et al. |
| 2020/0200776 | A1 | 6/2020 | Fesenko et al. |
| 2021/0000787 | A1* | 1/2021 | Chodoeva ............ A61K 9/0043 |

OTHER PUBLICATIONS

Chaaban, H. et al. (Jan. 3, 2017). "The photostability of flavanones, flavonols and flavones and evolution of their antioxidant activity," Journal of Photochemistry and Photobiology, A: Chemistry 336:131-139.
International Search Report dated Mar. 24, 2020 for PCT Application No. PCT/UA2019/000155, filed Dec. 17, 2019, 6 pages.
International Search Report dated Mar. 30, 2020 for PCT Application No. PCT/UA2019/000156, filed Dec. 17, 2019, 6 pages.
Invitation to Pay Additional Fees dated Apr. 15, 2020, for PCT Application No. PCT/UA2019/000157, filed on Dec. 17, 2019, 17 pages.
Kakkar, S. et al. (Jan. 1, 2014). "A Review on Protocatechuic Acid and Its Pharmacological Potenital," Pharmacology, 9 pages.
Kakran, M. et al. (2011). Colloids and Surface B: Biointerfaces 88:121-130.
Makris, D.P. et al. (Jul. 1, 2001). "Comparison of Quercetin and a Non-Orthohydroxy Flavonol as Antioxidants by Competing in Vitro Oxidation Reactions," Journal of Agricultural and Food Chemistry 49(7):3370-3377.
Rafiei, H. et al. (Jun. 5, 2019, e-published May 24, 2019). "Phenolic Breakdown Products of Cyanidin and Quercetin Contribute to Protection Against Mitochondrial Impairment and Reactive Oxygen Species Generation in an In Vitro Model of Hepatocyte Steatosis," Journal of Agricultural and Food Chemistry 67(22):6241-6247.
Ramesova, S. et al. (Jan. 2012, e-published Nov. 6, 2011). "On the Stability of the Bioactive Flavonoids Quercetin and Luteolin Under Oxygen-Free Conditions," Anal Bioanal Chem 402(2):975-982.
Scalia, S. et al. (May 13, 2013, e-published Mar. 26, 2013). "Quercetin solid lipid microparticles: A flavonoid for inhalation lung delivery," Eur. J Pharm Sci.49(2): 278-285.
Schulze, B et al. (Jun. 2014). Food Science and Technology 57:426-433.
Written Opinion dated Mar. 24, 2020 for PCT Application No. PCT/UA2019/000155, filed Dec. 17, 2019, 9 pages.
Written Opinion dated Mar. 30, 2020 for PCT Application No. PCT/UA2019/000156, filed Dec. 17, 2019, 9 pages.
Zenkevich, I.G. et al. (Mar. 27, 2007). "Identification of the Products of Oxidation of Quercetin by Air Oxygen at Ambient Temperature," Molecules 12(3):654-672.
Bhouri et al. "Investigation of the apoptotic way induced by digallic acid in human lymphoblastoid TK6 cells." Cancer Cell International 12: 26 (2012).
Bhouri et al. "Digallic acid from *Pistascia lentiscus* fruits induces apoptosis and enhances antioxidant activities." Phytother. Res. 26: 387-391 (2012).
Dachineni et al. "Salicylic acid metabolites and derivatives inhibit CDK activity: Novel insights into aspirin's chemopreventive effects against colorectal cancer." International Journal of Oncology 51: 1661-1673 (2017).
R. Denina. "Heart Failure Treatment in Patients With Recurrent Myocardial Infarction." The Pharma Innovation Journal 2(1): 30-35(2013).
Graefe et al. "Pharmacokinetics and Bioavailability of Quercetin Glycosides in Humans." J Clin Pharmacol 41: 492-499 (2001).
Harwood et al. "A Critical Review of the Data related to the Safety of Quercetin and lack of evidence of in vivo toxicity, including lack of Genotoxic/Carcinogenic Properties." Food and Chemical Toxicology 45: 2179-2205 (2007).
Kamaya et al. "Acute Toxicity of Benzoic Acids to the Crustacean Daphnia magna." Chemosphere 59: 255-261 (2005).
Kuzmenko et al. "Experimental therapy of cardiac remodeling with quercetin-containing drugs." Pathological Physiology and Experimental Therapy: 17-22 (2011).
Lee et al. "Toxicity and quantitative structure-activity relationships of benzoic acids to Pseudokirchneriella subcapitata." Journal of Hazardous Materials 165: 156-161 (2009).
Martins et al. "Assays with Daphnia magna and Danio rerio as alert systems in aquatic toxicology." Environment International 33: 414-425 (2007).
Nakamura et al. "Toxic Dose of a Simple Phenolic Antioxidant, Protocatechuic Acid, Attenuates the Glutathione Level in ICR Mouse Liver and Kidney." J. Agric. Food Chem. 49: 5674-5678 (2001).
S. Parasuraman. "Toxicological screening." Journal of Pharmacology and Pharmacotherapeutics 2(2): 74-79 (2011).
Pashevin et al. "Antiatherogenic effect of quercetin is mediated by proteasome inhibition in the aorta and circulating leukocytes." Pharmacological Reports 63: 1009-1018 (2011).
Porcu et al. "Aqueous injection of quercetin: An approach for confirmation of its direct in vivo cardiovascular effects." International Journal of Pharmaceutics 541: 224-233 (2018).
Roos et al. "Chronic senolytic treatment alleviates established vasomotor dysfunction in aged or atherosclerotic mice." Aging Cell 15(5): 973-7 (2016).
Ryzhkova et al. "Korvitin Reduces the High Maintenance of Myeloperoxidase in Plasma of Blood of Patients with the Acute Infarct of Myocardium." Fiziol Zh. 62(2): 87-93 (2016).
Salem et al. "In vitro anti-uveal melanoma activity of phenolic compounds from the Egyptian medicinal plant *Acacia nilotica*." Fitoterapia 82: 1279-1284 (2011).
J. Straub. "Environmental risk assessment for new human pharmaceuticals in the European Union according to the draft guideline/discussion paper of Jan. 2001." Toxicology Letters 131: 137-143 (2002).
Wang et al. "Cytotoxic Activity of Sesquiterpenoids from Atractylodes ovata on Leukemia Cell Lines." Planta Med 68: 204-208 (2002).
Wang et al. "The biological activities, chemical stability, metabolism and delivery systems of quercetin: A review." Trends in Food Science & Technology 56: 21-38 (2016).
Xie et al. "Protocatechuic acid inhibits the growth of ovarian cancer cells by inducing apoptosis and autophagy." Phytotherapy Research : 1-8 (2018).
Xu et al. "Senolytics improve physical function and increase lifespan in old age." Nature Medicine 24(8), 1246-1256 (2018).
Yin et al. "Apoptotic Effects of Protocatechuic Acid in Human Breast, Lung, Liver, Cervix, and Prostate Cancer Cells: Potential Mechanisms of Action." J. Agric. Food Chem. 57: 6468-6473 (2009).

* cited by examiner

| relative retention time | Name | Chemical structure | UV spectra (200-500 nm) |
|---|---|---|---|
| 0.30 | 3,4-dihydroxybenzoic acid (protocatechuic acid) | 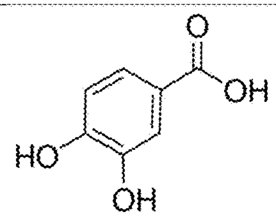 | |
| 1.0 | quercetin | 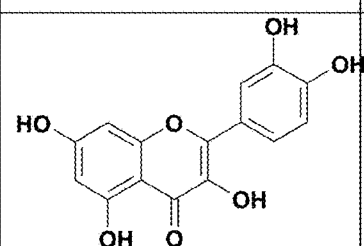 | |

FIG. 5

| relative retention time * | Name | Chemical structure | UV spectra (200-500 nm) |
|---|---|---|---|
| 0.34* | 2,4,6-trihydroxybenzoic acid | 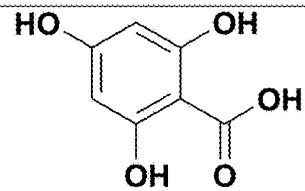 | |
| 1.0 | quercetin | 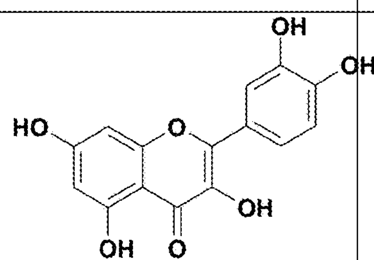 | |

*- relative to quercetin

FIG. 10

| retention time, min | relative retention time * | content, % | UV- spectra (200-500 nm) |
|---|---|---|---|
| 9.84 | 0.77 | 6.43 | |
| 12.79 (quercetin) | 1.0 | 89.49 | |

*- relative to quercetin peak.

FIG. 15

METHODS OF MONITORING SAFETY OF QUERCETIN COMPOSITIONS

FIELD OF INVENTION

The invention relates to methods of monitoring safety of quercetin compositions. More specifically, the methods relate to the determination of unsafe levels of contaminant in quercetin compositions.

BACKGROUND

Quercetin is a plant flavonoid whose inclusion in human diet has been widely associated with a number of health benefits. These benefits include: 1) antioxidant; 2) anti-inflammatory; 3) antiviral; and 4) anticancer activities (Wang et al., 2016). Quercetin is also used to ease cardiovascular diseases (i.e., heart disease, hypertension, and high blood cholesterol). Recently, quercetin was shown to slow down or even reverse aging in animals by targeting senescent cells (i.e. being so called "senolytic drug") (Xu et al., 2018) (Roos et al., 2016). In the US and elsewhere quercetin is a popular dietary supplement sold as powder or liquids.

The bioavailability of quercetin in humans is low and highly variable (0-50%), and it is rapidly cleared with an elimination half-life of 1-2 hours after ingestion in foods or supplements (Graefe et al., 2001). There are several delivery systems to increase quercetin bioavailability: 1) lipid-based carriers; 2) polymer-based carriers or nanoparticles; 3) inclusion complexes; 4) micelles; and 5) conjugates-based capsulations (Wang et al., 2016). One such polymer-based carrier is polyvinylpyrrolidone (PVP). One PVP-based formulation of quercetin provides a 20,000-fold increase in quercetin solubility (Porcu et al., 2018).

CORVITIN® (PJSC SIC "Borshchahivskiy CPP", Kiev, Ukraine), which combines quercetin with PVP in solid form, is suitable for intravenous injections when dissolved in saline. Quercetin/PVP formulations lower blood pressure in rats both in short-term and long-term bases (Porcu et al., 2018). Prolonged administration (1 month) of CORVITIN® to rabbits following a cholesterol-rich diet significantly decreased atherosclerotic lesion areas in the aorta (Pashevin et al., 2011). CORVITIN® treatment improves cardiac hemodynamics. CORVITIN® treatment also reduces cardiac fibrosis (Kuzmenko et al., 2013).

CORVITIN® administered to patients with acute myocardial infarction decreases the activity of myeloperoxidase in plasma of blood, which is a marker of the metabolic activity of phagocytes and inflammation (Ryzhkova et al., 2016). CORVITIN® treatment results in decreased blood pressure, pulse pressure, improved structural and functional characteristics of the myocardium (including the increase in ejection fraction (EF), and significant decrease of left ventricular end-diastolic dimension (LVEDd), end-diastolic volume (EDV), left ventricular mass index (LVMI), reduced NT-proBNP levels, total NO and improved heart rate variability (Denina, 2013). CORVITIN® is approved in the Ukraine for therapy in patients suffering myocardial infarction and related diseases.

Lyophilization of drugs, particularly biopharmaceuticals, is often used when a drug ingredient is unstable in liquid or frozen form. In addition, lyophilization allows the storage of material for longer periods of time and at room temperature.

Appropriate drug storage conditions are important for safe and efficient drug application, and monitoring of formation of toxic contaminants during storage is especially critical. No studies on the stability of lyophilized quercetin compositions and monitoring safety of its byproducts have been performed previously.

SUMMARY

Provided herein are methods of assessing safety of a quercetin composition by determining the level of a contaminant in the quercetin composition. In various embodiments, the contaminant is 3,4-dihydroxybenzoic acid (protocatechuic acid); 2,4,6-trihydroxybenzoic acid, or 2-(3,4-dihydroxybenzoyloxy)-4,6-dihydroxybenzoic acid. The quercetin composition is identified as unsafe if the level of protocatechuic acid; 2,4,6-trihydroxybenzoic acid, or 2-(3,4-dihydroxybenzoyloxy)-4,6-dihydroxybenzoic acid is above a threshold level. The quercetin composition is identified as not unsafe if the level of protocatechuic acid; 2,4,6-trihydroxybenzoic acid, or 2-(3,4-dihydroxybenzoyloxy)-4,6-dihydroxybenzoic acid is below the threshold level.

In an embodiment, the threshold level of protocatechuic acid is about 0.6%, about 0.5%, about 0.4%, about 0.3%, or about 0.2% (w/w) of protocatechuic acid/quercetin. In some embodiments, the threshold level of protocatechuic acid is about 0.14%, about 0.13%, about 0.12%, about 0.11%, or about 0.10% (w/w) of protocatechuic acid/quercetin. In some embodiments, the threshold level of protocatechuic acid is about 0.12±0.02% (w/w) of protocatechuic acid/quercetin.

In an embodiment, the threshold level of 2,4,6-trihydroxybenzoic acid is about 0.17%, about 0.16%, about 0.15%, about 0.14%, about 0.13%, about 0.12%, about 0.11%, about 0.10%, about 0.09%, or about 0.08% (w/w) 2,4,6-THBA/quercetin. In some embodiments, the threshold level of 2,4,6-trihydroxybenzoic acid is about 0.07%, about 0.06%, about 0.05%, about 0.04%, about 0.03% (w/w) of 2,4,6-trihydroxybenzoic acid/quercetin. In some embodiments, the threshold level of 2,4,6-trihydroxybenzoic acid is about 0.05±0.02% (w/w) of 2,4,6-trihydroxybenzoic acid/quercetin.

In an embodiment, the threshold level of 2-(3,4-dihydroxybenzoyloxy)-4,6-dihydroxybenzoic acid is about 2%, about 1.5%, about 1%, about 0.9%, about 0.8%, about 0.7% or about 0.6% (w/w) of 2-(3,4-dihydroxybenzoyloxy)-4,6-dihydroxybenzoic acid/quercetin. In some embodiments, the threshold level of 2-(3,4-dihydroxybenzoyloxy)-4,6-dihydroxybenzoic acid is about 0.54%, about 0.53%, about 0.52%, about 0.51%, about 0.50%, about 0.49%, or about 0.48% (w/w) of 2-(3,4-dihydroxybenzoyloxy)-4,6-dihydroxybenzoic acid/quercetin. In some embodiments, the threshold level of 2-(3,4-dihydroxybenzoyloxy)-4,6-dihydroxybenzoic acid is about 0.51±0.03% (w/w) of 2-(3,4-dihydroxybenzoyloxy)-4,6-dihydroxybenzoic acid/quercetin.

Also provided herein are methods of assessing safety of a quercetin composition by determining a level of at least two contaminants in the quercetin composition. In various embodiments, the contaminants are two or more of protocatechuic acid, 2,4,6-trihydroxybenzoic acid, and 2-(3,4-dihydroxybenzoyloxy)-4,6-dihydroxybenzoic acid. The quercetin composition is identified as unsafe if the level of the at least two contaminants is above the threshold level. The quercetin composition is identified as not unsafe if the level of the at least two contaminants is below the threshold level. In an embodiment, the threshold level is 1 and calculated for the contaminants determined by the equation: (% (w/w) of protocatechuic acid/quercetin)/T1+(% (w/w) of 2,4,6-trihydroxybenzoic acid/quercetin)/T2+(% (w/w) of 2-(3,4-dihydroxybenzoyloxy)-4,6-dihydroxybenzoic acid/quercetin)/T3; wherein T1 is the threshold level of protocatechuic acid, T2 is the threshold level of 2,4,6-trihydroxybenzoic acid, and T3 is the threshold level of 2-(3,4-dihydroxybenzoyloxy)-4,6-dihydroxybenzoic acid/quercetin; and, wherein for a contaminant not selected to be determined, the contribution to the threshold level is zero.

In some embodiments, the threshold level is 1 and calculated for the contaminants determined by the equation: (% (w/w) of protocatechuic acid/quercetin)/0.65+(% (w/w) of 2,4,6-trihydroxybenzoic acid/quercetin)/0.33+(% (w/w) of 2-(3,4-dihydroxybenzoyloxy)-4,6-dihydroxybenzoic acid/quercetin)/2.6. For a contaminant not selected to be determined, the contribution to the threshold level is zero.

Also provided herein are methods for reducing the rate of formation of protocatechuic acid by degradation of a solid form quercetin composition by (1) purging air from an airtight container containing the solid form quercetin composition and filling the container with an atmosphere consisting essentially of an inert gas or a combination of inert gases and (2) assessing the safety of the solid form quercetin composition according to any of the methods above.

In some embodiments, the quercetin composition is a pharmaceutically acceptable composition. In some embodiments, the quercetin composition is formulated to be administered parenterally, intravenously, intraarterially, intramuscularly, intradermally, transdermally, intraperitoneally or subcutaneously. In some embodiments, the quercetin composition includes a solid form quercetin composition. In some embodiments, the solid form quercetin composition is freeze-dried quercetin. In some embodiments, the solid form quercetin composition is prepared by spray drying, rotoevaporation, or crystallization.

In some embodiments, the quercetin composition includes a drug delivery formulation. In some embodiments, the drug delivery formulation includes a lipid-based carrier, a polymer-based carrier, nanoparticles, inclusion complexes, micelles, or a conjugate-based capsulation. In some embodiments, the drug delivery formulation includes a lipid-based carrier and the lipid-based carrier is glycerin, propylene glycol, stearate, or olive oil. In some embodiments, the drug delivery formulation includes a polymer-based carrier and the polymer-based carrier comprises polyvinylpyrrolidone. In some embodiments, the quercetin composition includes about 8:1, about 9:1, about 10:1, about 11:1, or about 12:1 polyvinylpyrrolidone:quercetin w/w. In some embodiments, the quercetin composition includes 7-11% quercetin and 89-93% polyvinylpyrrolidone w/w.

In some embodiments, the level of a contaminant in the quercetin composition is determined by chromatography. In some embodiments, the chromatography is liquid chromatography; thin layer chromatography; gas chromatography; or electrophoresis. In some embodiments, the liquid chromatography includes high-performance (HPLC) or ultra performance (UPLC) liquid chromatography. In some embodiments, the method further includes ultraviolet, diode-array, mass, evaporating light scattering, conductometric, electrochemical, or fluorescence detection. In some embodiments, the chromatography is gas chromatography and further includes flame-ionizing or mass detection.

Provided herein are methods of assessing safety of a quercetin composition by determining a 48 h-EC50 for the quercetin composition in a *Daphnia magna* mobility assay and comparing the 48 h-EC50 to a threshold level. The quercetin composition is identified as unsafe if the 48 h-EC50 is below the threshold level and not unsafe if the 48 h-EC50 is above the threshold level. In some embodiments the threshold level is about 1 mg/L and other embodiments the threshold level is about 0.5 mg/L.

Provided herein are methods of assessing safety of a quercetin composition by determining a 72 h-EC50 in a cytotoxicity assay using MDA-MB231 human breast cancer cells and comparing the 72 h-EC50 to a threshold level. The quercetin composition is identified as unsafe if the 72 h-EC50 is below the threshold level and not unsafe if the 72 h-EC50 is above the threshold level. In some embodiments the threshold level is about 7.5 mg/ml and other embodiments the threshold level is about 750 micrograms/ml.

In some embodiments, the quercetin composition is a pharmaceutically acceptable composition. In some embodiments, the quercetin composition is formulated to be administered parenterally, intravenously, intraarterially, intramuscularly, intradermally, transdermally, intraperitoneally or subcutaneously. In some embodiments, the quercetin composition includes a solid form quercetin composition. In some embodiments, the solid form quercetin composition is freeze-dried quercetin. In some embodiments, the solid form quercetin composition is prepared by spray drying, rotoevaporation, or crystallization.

In some embodiments, the quercetin composition includes a drug delivery formulation. In some embodiments, the drug delivery formulation includes a lipid-based carrier, a polymer-based carrier, nanoparticles, inclusion complexes, micelles, or a conjugate-based capsulation. In some embodiments, the drug delivery formulation includes a lipid-based carrier and the lipid-based carrier is glycerin, propylene glycol, stearate, or olive oil. In some embodiments, the drug delivery formulation includes a polymer-based carrier and the polymer-based carrier comprises polyvinylpyrrolidone. In some embodiments, the quercetin composition includes about 8:1, about 9:1, about 10:1, about 11:1, or about 12:1 polyvinylpyrrolidone:quercetin w/w. In some embodiments, the quercetin composition includes 7-11% quercetin and 89-93% polyvinylpyrrolidone w/w.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 3A is HPLC-Mass Spectrometry results (LC (upper trace) and mass spectrum (lower trace)) of solid form quercetin stored for 18 months at 20-25° C. having a peak with a retention time 3.93 min yielding a peak with a molecular ion mass m/z=153 observed using Q3 mode. FIG. 3B is HPLC-Mass Spectrometry results (LC (upper trace) and mass spectrum (lower trace)) of fragmentation of the molecular ion m/z=153 using EPI mode, negative polarity, collision energy −10 V-30 V yielding another peak with m/z=109;

FIG. 5 shows retention times, relative content and UV spectra for protocatechuic acid and quercetin;

FIG. 10 shows retention times and UV spectra for 2,4,6-trihydroxybenzoic acid and quercetin;

FIG. 15 shows retention times, relative content and UV spectra for 2-(3,4-dihydroxybenzoyloxy)-4,6-dihydroxybenzoic acid and quercetin;

DETAILED DESCRIPTION

Figure 1:
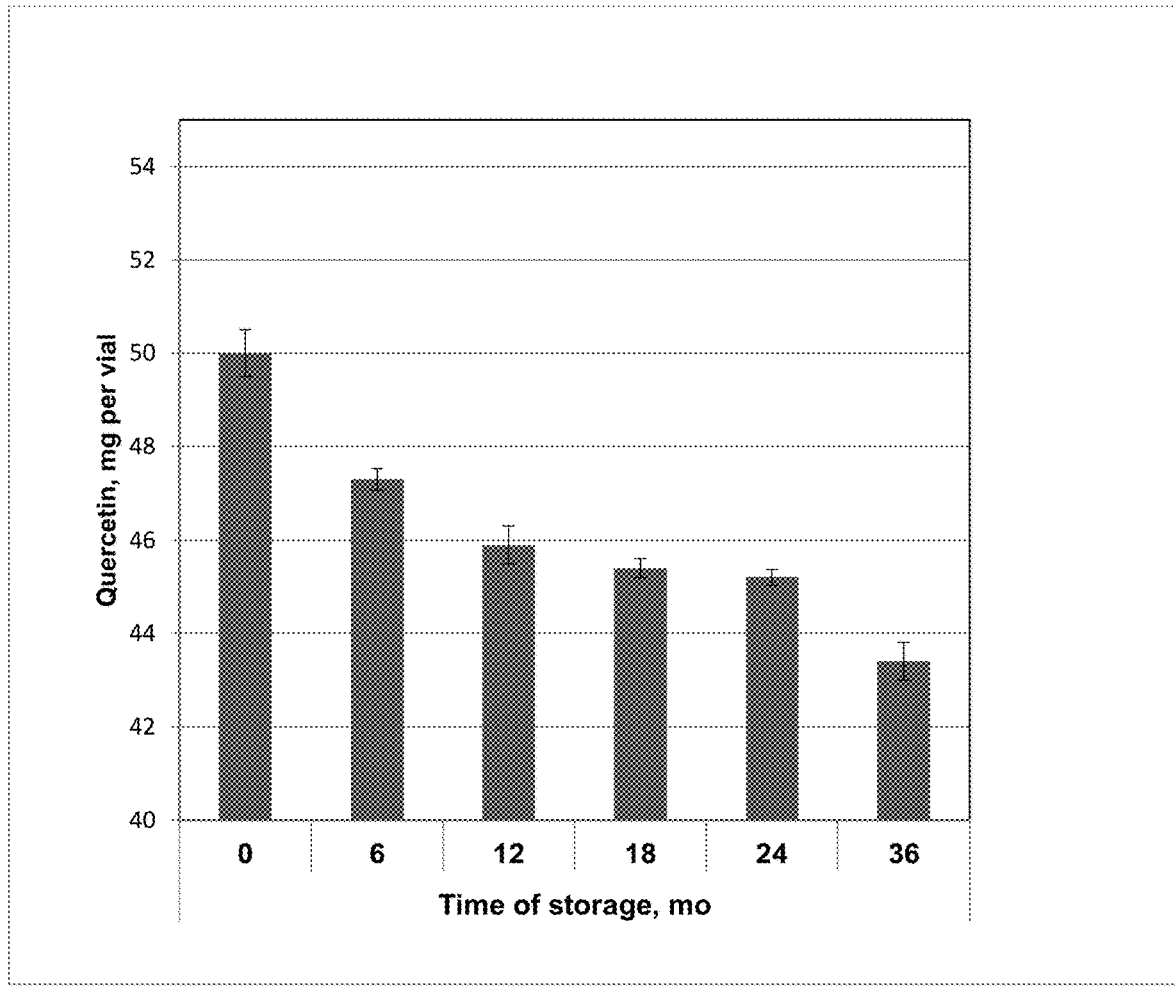
FIG. 1 shows degradation of solid form quercetin composition in air atmosphere under ambient temperature conditions over time.

Provided herein are methods of assessing safety of quercetin compositions including determining the levels of contaminants that form upon the degradation of quercetin compositions. Embodiments of the invention can increase patient safety.

Applicant surprisingly found that solid form quercetin compositions undergo degradation under ambient storage conditions in air. Applicant therefore developed assays to identify, characterize and quantify products of such degradation. Three major products of quercetin degradation include 3,4-dihydroxybenzoic acid (protocatechuic acid), 2,4,6-trihydroxybenzoic acid, and 2-(3,4-dihydroxybenzoyloxy)-4,6-dihydroxybenzoic acid.

All three contaminants have demonstrated toxicity in in vitro and in vivo assays. Assessment of safety of quercetin composition based on quantification of levels of protocatechuic acid, 2,4,6-trihydroxybenzoic acid, 2-(3,4-dihydroxybenzoyloxy)-4,6-dihydroxybenzoic acid is therefore provided herein.

Quercetin, 2-(3,4-dihydroxyphenyl)-3,5,7-trihydroxy-4H-chromen-4-one, is a plant flavonoid. Quercetin compositions include relatively pure form quercetin and those that include delivery formulations. Drug delivery refers to approaches, formulations, technologies, and systems for transporting a pharmaceutical compound in the body as needed to safely achieve its desired therapeutic effect. Drug delivery formulations for quercetin can include 1) lipid-based carriers; 2) polymer-based carriers or nanoparticles; 3) inclusion complexes; 4) micelles; and 5) conjugate-based capsulations (Wang et al., 2016). Liquid quercetin compositions include formulations with glycerin, propylene glycol, stearate, or olive oil.

In some embodiments solid form quercetin compositions are formulated to be administered orally. In other embodiments liquid form quercetin compositions can be provided as solutions, capsules, or aerosols comprising glycerin, propylene glycol, stearate, or olive oil. These compositions can be formulated to be administered parenterally, intravenously, intraarterially, intramuscularly, intradermally, transdermally, intraperitoneally or subcutaneously.

In some embodiments, quercetin compositions include the polymer-based carrier polyvinylpyrrolidone (PVP). In some embodiments, the ratio of PVP:quercetin can be about 8:1, about 9:1, about 10:1, about 11:1, or about 12:1 PVP:quercetin. The relative proportions can vary by about 1%, 2%, 3% or 4%. PVP average molecular weights include, but are not limited to, 8,000, 10,000, or 40,000 g/mol.

In some embodiments, the quercetin composition is in solid form. The solid form of a quercetin composition can be lyophilized (freeze-dried). The solid form of a quercetin composition can be obtained by spray-drying, rotoevaporation or crystallization. When solvent is removed by rotary evaporation, an agglomerated intermediate product is produced, which can be deagglomerated to provide a dry formulation of the quercetin composition. The solid form of a quercetin composition can be provided as a powder, capsules, granules and tablets comprising gelatin, cellulose, silica, or rice powder. In some embodiments, the quercetin composition can be about 9±2% quercetin and about 91±2% polyvinylpyrrolidone w/w in a lyophilizate.

The solution of the quercetin composition can be sterilized with a sterilizing filter prior to preparing the solid form quercetin composition. Typically, this will involve filtering the solution using a 0.2 micron filter that is solvent compatible, to make a sterile solution. The sterile solution can then be aliquoted directly into dose-sized sterile vials or may be aliquoted at a later time, such as in a sterile fill.

A suitable lyophilization cycle can be readily determined by those skilled in the art, as lyophilization conditions may vary. For example, primary drying conditions may vary from −50° C. to −5° C. The length of the cycle is generally known to those skilled in the art, for example, the cycle length may vary from 8 to 48 hours, generally, sufficient time to remove the solvent or liquid from the product. The secondary drying conditions may vary from 0° C. to 50° C.

Quercetin compositions as a lyophilized powder in an air atmosphere were found to undergo time-dependent degradation with a rate of about 2% per year at room temperature (see Example 2).

Methods for the measurement of quercetin, such as by UV spectroscopy, are known in the art. For example, a solid form quercetin composition is dissolved in 96% v/v analytical grade ethanol and measured spectrophotometrically at 374 nm using 96% ethanol as blank control. In parallel, absorbance of reference solutions (with known quercetin concentrations) are measured. Quercetin content is determined by method of standards comparison.

Quercetin degradation leads to formation of several contaminants (see Example 3). The contaminants are known toxic compounds. Provided herein are methods for the detection and measurement of these contaminants to assess the safety of a quercetin composition. Methods for detection and measurement are known in the art and include, but are not limited to, chromatography. Chromatography is the separation of a mixture by passing it in solution or suspension or as a vapor (as in gas chromatography) through a medium in which the components move at different rates. Chromatographic methods include liquid chromatography; thin layer chromatography; gas chromatography; or electrophoresis. Liquid chromatography includes high-performance (HPLC) and ultraperformance (UPLC) liquid chromatography. Detection of the separated components include ultraviolet (UV), diode-array (DAD), mass (MS/MS), evaporating light scattering (ELS), conductometric (SD), electrochemical (EC), and fluorescence detection (FD). Gas chromatography can include flame-ionizing detection (FID) or mass detection (MS/MS).

Consequently, provided herein are methods to determine the safety of a quercetin composition by measuring the level of at least one of its contaminants and comparing it to a threshold level. If the level of the contaminant is above the threshold level, then the quercetin composition is deemed unsafe. Unsafe means the quercetin composition is potentially toxic with respect to the tested contaminant. If the level of the contaminant is below the threshold level, then the quercetin composition is deemed not unsafe. Not unsafe means that the quercetin composition is unlikely to be potentially toxic with respect to the tested contaminant. Individual samples or manufacturing lots of a quercetin composition identified as unsafe can be quarantined.

Also provided are methods for reducing the rate of formation of contaminants by degradation of a solid form quercetin composition by (1) purging air from an airtight container containing the solid form quercetin composition and filling the container with an atmosphere consisting essentially of an inert gas or a combination of inert gases and (2) assessing the safety of the solid form quercetin composition according to methods described above. Assessing the safety of the solid form quercetin composition can be performed after storage of the solid form quercetin composition for a certain period of time. The assessment can be performed after at least one day, at least one week, at least one months, at least 3 months, at least six months, at least nine months, at least one year, at least 18 months, at least two years, at least 30 months, at least 3 years, at least 4 years, or at least 6 years of storage. The storage temperature can be about 21° C., about 20-25° C., or about 15-30° C.

In some embodiments, the contaminant includes protocatechuic acid (PCA). Consequently, provided herein are methods for detecting and measuring the level of PCA in quercetin compositions. Also provided are methods to determine the safety of a quercetin composition by measuring the level of PCA and comparing it to a threshold level. If the level of PCA is above the threshold level, then the quercetin composition is deemed unsafe. If the level of PCA is below the threshold level, then the quercetin composition is deemed not unsafe.

Figure 2:
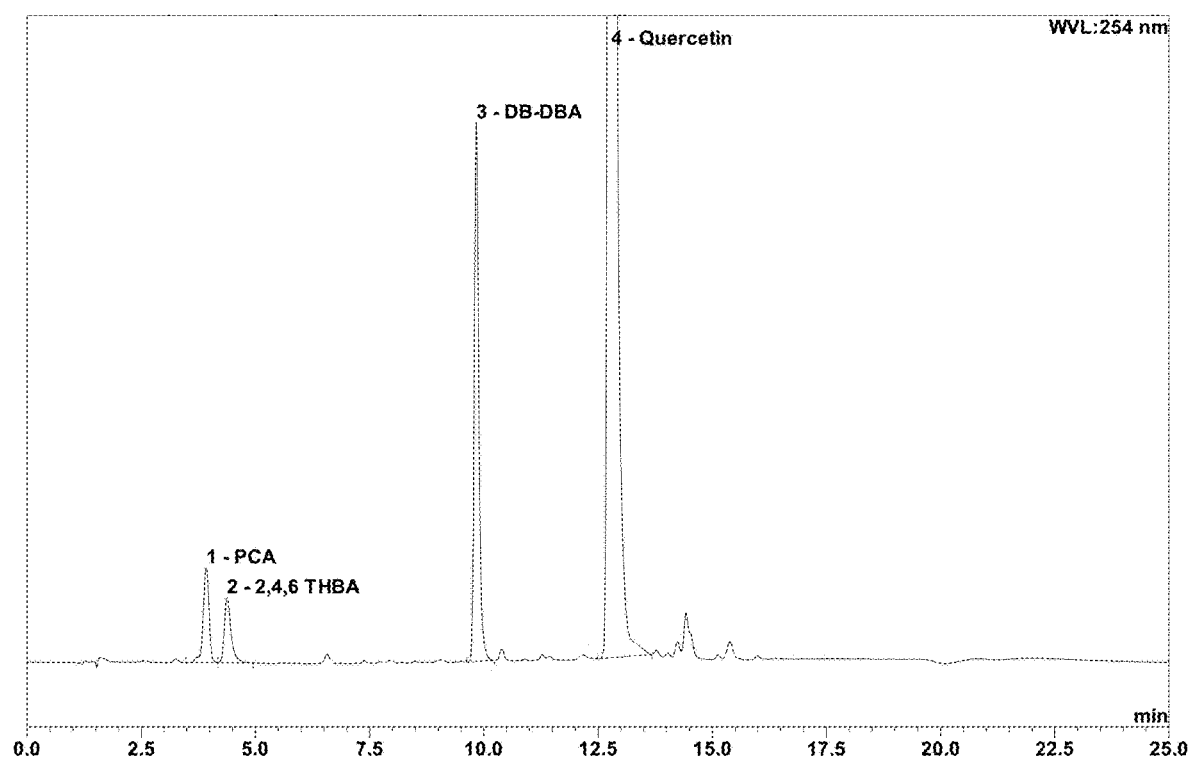
FIG. 2 shows chromatographic detection of degradation products of solid form quercetin.

Methods to detect PCA are known in the art, such as by liquid chromatography with UV detection. For example, a solution containing PCA is subjected to liquid chromatography using gradient elution with the following conditions: stainless steel column with stationary phase end-capped octadecylsilyl silica for chromatography R; size (150×3.9) mm, particle size 5 micron. Mobile phase A: 0.1% phosphoric acid v/v; mobile phase B—methanol; column temperature: 25° C.; flow rate: 1 mL/min.; UV detection at 254 nm. Relative retention time is 1.00 for quercetin, and 0.34 for PCA (FIG. 2). Content of PCA relative to quercetin can be calculated by formula (in percentage):

$$X_i = \frac{S_i}{S_0},$$

where: $S_i$—peak area of PCA on the chromatogram of test solution;
$S_0$—peak area of quercetin on the chromatogram reference solution (a);

Protocatechuic acid (PCA) is a toxic compound. Methods to determine toxicity of compounds are known in the art. They include, but are not limited to, in vitro assays for mutagenicity/carcinogenicity (e.g. Ames test in bacteria) and in vitro cytotoxicity (e.g., MTT (e.g. (Dachineni et al., 2017)), XTT, INT or MTS assay, SRB or WST-1 assay in mammalian cells). A label-free approach to follow the cytotoxic response of adherent animal cells is electric cell-substrate impedance sensing (ECIS). Acute and chronic toxicity in rodents and non-human primates can also be used (Parasuraman, 2011). Toxicity of water-soluble compounds can be assessed by appropriate model systems of aquatic organisms such as alga, crustacean, fishes and others (Straub, 2002).

PCA is toxic in a range of assays. PCA causes apoptosis (DNA fragmentation, caspase 3 activation) in HeLa, MCF7, HepG2, A549, LNCaP human cell lines at concentration 5-8 microM. It also causes loss of viability after 48 h in OVCAR3 and LNCaP human cell lines with EC50 5 microM (Yin et al., 2009) (Xie et al., 2018). In mice, subchronic administration of PCA (0.1% in drinking water for 60 days) causes hepatotoxicity (increase in ALT), and the same effect was with acute administration of 50 mg/kg intraperitoneally (Nakamura et al., 2001).

As an example, a container of CORVITIN® has 50 mg of quercetin, which is administered i.v. after dissolving with saline to a concentration of 1 mg/ml. Given that the levels protocatechuic acid formation after 12 months of quercetin storage under ambient conditions is above 0.4% of quercetin content (FIG. 6), the PCA concentration of the reconstituted quercetin composition is approximately 4 microgram/ml, or 26 micromolar. Such amount of PCA formed during quercetin degradation under ambient conditions is about 5-times higher than its EC50 for LNCaP cells (5 micromolar).

Figure 18:
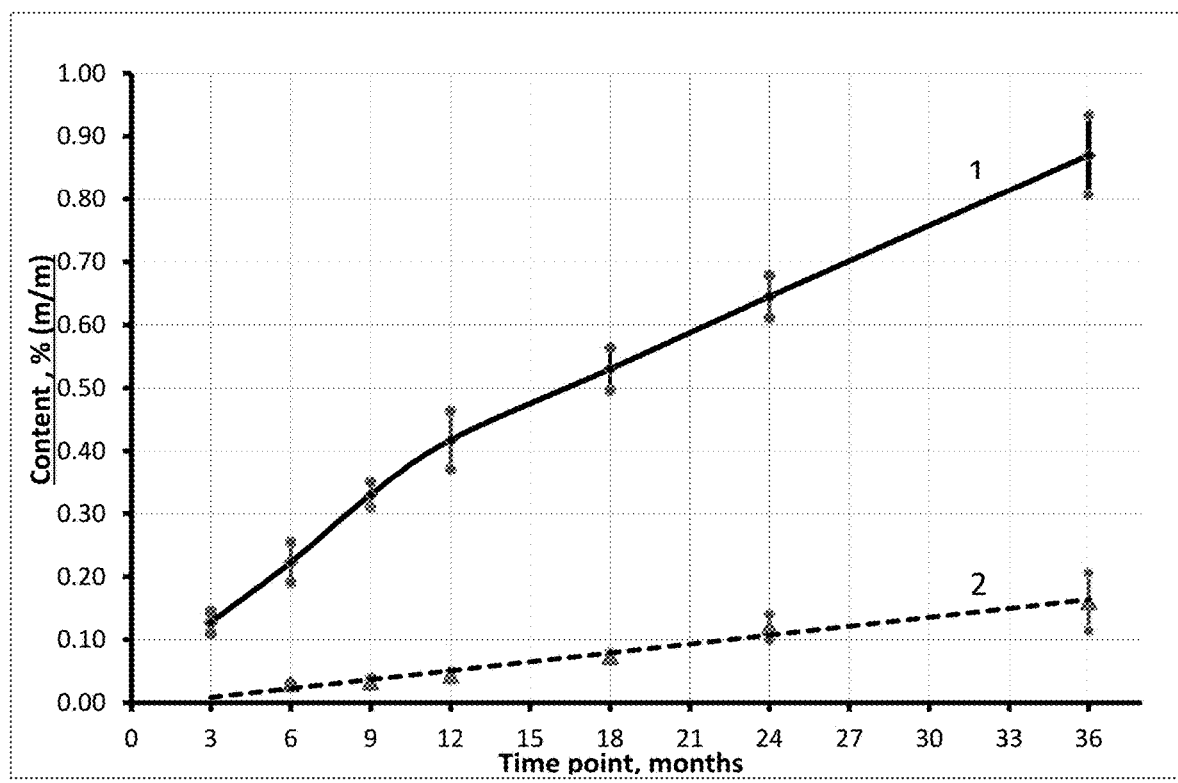
FIG. 18 shows effect of substitution of air with nitrogen gas storage atmosphere on formation of protocatechuic acid at ambient temperature.

Under nitrogen gas, protocatechuic acid formation after 24 months of CORVITIN® storage is much lower than when exposed to air, i.e. 0.12±0.02% versus 0.65±0.03% w/w (FIG. 18). Extensive clinical experience with CORVITIN® does not demonstrate any toxic effect of such preparations with these levels of protocatechuic acid.

In some embodiments, the quercetin composition is identified as unsafe if the level of PCA is above about 0.14% of quercetin (w/w) (weight/weight). It is known in the art that NOEL (no observable effect level) of chemicals is, on average, 5 times lower than EC50. In some embodiments, the quercetin composition is identified as not unsafe if the level of PCA is below about 0.12±0.02%. In certain embodiments, the threshold level PCA to determine a quercetin composition is unsafe/not unsafe is about 0.14%, about 0.12%, about 0.10%, or about 0.08% (w/w) PCA/quercetin. In certain embodiments, a quercetin composition is unsafe/not unsafe is about 0.6%, about 0.5%, about 0.4%, about 0.3%, or about 0.2% (w/w) PCA/quercetin.

Also provided are methods for reducing the rate of formation of PCA by degradation of a solid form quercetin composition by (1) purging air from an airtight container containing the solid form quercetin composition and filling the container with an atmosphere consisting essentially of an inert gas or a combination of inert gases and (2) assessing the safety of the solid form quercetin composition according to methods described above. Assessing the safety of the solid form quercetin composition can be performed after storage of the solid form quercetin composition for a certain period of time. The assessment can be performed after at least one day, at least one week, at least one months, at least 3 months, at least six months, at least nine months, at least one year, at least 18 months, at least two years, at least 30 months, at least 3 years, at least 4 years, or at least 6 years of storage. The storage temperature can be about 21° C., about 20-25° C., about 15-30° C.

Another degradation product of solid form quercetin compositions is a toxic compound, 2,4,6-trihydroxybenzoic acid (2,4,6-THBA). This toxic byproduct was not predicted by prior studies of quercetin degradation in solution (Wang et al., 2016).

Consequently, provided herein are methods for detecting and measuring the level of 2,4,6-THBA in quercetin compositions. Also provided are methods to determine the safety of a quercetin composition by measuring the level of 2,4,6-THBA and comparing it to a threshold level. If the level of 2,4,6-THBA is above the threshold level, then the quercetin composition is deemed unsafe. If the level of 2,4,6-THBR is below the threshold level, then the quercetin composition is deemed not unsafe.

Methods to detect 2,4,6-THBA are known in the art, such as by liquid chromatography with UV detection. For example, a solution containing 2,4,6-THBR is subjected to liquid chromatography using gradient elution with the following conditions: stainless steel column with stationary phase end-capped octadecylsilyl silica for chromatography R; size (150×3.9) mm, particle size 5 micron. Mobile phase A: 0.1% phosphoric acid v/v; mobile phase B—methanol; column temperature: 25° C.; flow rate: 1 mL/min.; UV detection at 254 nm. Relative retention time is 1.00 for quercetin, and 0.34 for 2,4,6-trihydroxybenzoic acid (FIG. 2). Content of 2,4,6-trihydroxybenzoic acid relative to quercetin can be calculated by formula (in percentage):

$$X_i = \frac{S_i}{S_0},$$

where: $S_i$—peak area of 2,4,6-THBA on the chromatogram of test solution;
$S_0$—peak area of quercetin on the chromatogram reference solution (a).

2,4,6-THBA is toxic to a range of organisms. 2,4,6-THBA has a strong inhibitory effect on cyclin-dependent kinases CDK1, 2, 4, 6, which are key regulators of cell cycle. 2,4,6-THBA exhibits stronger inhibition of purified CDKs in vitro than other salicylic acid metabolites (Dachineni et al., 2017). 2,4,6-THBA is also more cytotoxic to HCT-116 human cells compared to other salicylic acid metabolites (Dachineni et al., 2017). Thus, 2,4,6-THBA is toxic to mammalian cells when tested in vitro.

2,4,6-THBR is a metabolite of benzoic acid. As judged by suppression of growth of *Pseudokirchneriella subcapitata*, a common biological indicator used most extensively by ecotoxicologists, benzoic acid has low toxicity (EC50 is 36 mg/l). In contrast, the EC50 of 2,4,6-THBA is 0.546 mg/l, which is 70-times higher than benzoic acid and its other derivatives (Lee and Chen, 2009). Similarly, benzoic acid demonstrates a low toxicity (860 mg/l EC50 at 48 h), but toxicity of 2,4,6-THBA is about 500 times higher (1.7 mg/l) in a *Daphnia magna* mobility assays (Kamaya et al., 2005)

Potential human toxicity of 2,4,6-THBA can be related to its toxicity based on studies with *Daphnia*. Toxicity of various compounds in *Daphnia* (48 h immobilization test) correlated to toxicity in humans (determined as reference dose for human oral exposure, RfD) (Martins et al., 2007). Given EC50 of 2,4,6-THBA for *Daphnia* is 1.7 mg/l, the RfD is estimated to be 0.02 mg/kg/day. For comparison, RfD for 2,4,6-THBA is more than 50-times higher than for benzoic acid (1 mg/kg/day), or 700 times higher than toxicity of quercetin (more than 15 mg/kg/day) in humans (Harwood et al., 2007). 2,4,6-THBA formed as a product of quercetin degradation is therefore toxic to humans.

Given that the levels of 2,4,6-THBA formation after 24 months of quercetin storage under ambient conditions is 0.33% of quercetin content, the 2,4,6-THBA concentration is approximately 3.5 ug/ml, or 3.5 mg/l. Such concentration of 2,4,6-THBA is about 2-times higher than the LC50 in 48 h for a *Daphna magna* immobilization test (1.7 mg/l). Air substitution with nitrogen gas decreases 2,4,6-THBA concentration 7-fold, to 0.05% (FIG. 19) or 0.5 mg/l, which is more than 3-times lower than LC50 in 48 h for a *Daphna* immobilization test (1.7 mg/l). Thus, the amount of 2,4,6-THBA formed from a solid form composition in air during storage conditions is toxic, and substituting air with nitrogen gas reduces 2,4,6-THBA formation to below toxic levels.

In some embodiments, the quercetin composition is identified as unsafe if the level of 2,4,6-THBA is above 0.07% of quercetin (w/w). In some embodiments, the quercetin composition is identified as not unsafe if the level of 2,4,6-THBA is below 0.05±0.02%. In certain embodiments, the threshold level 2,4,6-THBA to determine a quercetin composition is unsafe/not unsafe is about 0.07%, about 0.06%, about 0.05%, about 0.04%, about 0.03% (w/w) 2,4,6-THBA/quercetin. In certain embodiments, the threshold level 2,4,6-THBA to determine a quercetin composition is unsafe/not unsafe is about 0.17%, about 0.16%, about 0.15%, about 0.14%, about 0.13%, about 0.12%, about 0.11%, about 0.10%, about 0.09%, or about 0.08% (w/w) 2,4,6-THBA/quercetin. In certain embodiments, the threshold level 2,4,6-THBA to determine a quercetin composition is unsafe/not unsafe is about 0.30%, about 0.25%, or about 0.20% (w/w) 2,4,6-THBA/quercetin.

As noted above, one can observe toxicity of a quercetin composition that is contaminated by 2,4,6-THBA. Consequently, also provided herein are methods of assessing the safety of a quercetin composition by determining a 48 h-EC50 for the quercetin composition in a *Daphnia magna* mobility assay and comparing the 48 h-EC50 to a threshold level. The quercetin composition is identified as unsafe if the 48 h-EC50 is below the threshold level and not unsafe if the 48 h-EC50 is above the threshold level. In some embodiments the threshold level is about 1 mg/L and other embodiments the threshold level is about 0.5 mg/L.

Also provided are methods for reducing the rate of formation of 2,4,6-THBA by degradation of a solid form quercetin composition by (1) purging air from an airtight container containing the solid form quercetin composition and filling the container with an atmosphere consisting essentially of an inert gas or a combination of inert gases and (2) assessing the safety of the solid form quercetin composition according to methods described above. Assessing the safety of the solid form quercetin composition can be performed after storage of the solid form quercetin composition for a certain period of time. The assessment can be performed after at least one day, at least one week, at least one months, at least 3 months, at least six months, at least nine month, at least one year, at least 18 months, at least two years, at least 30 months, at least 3 years, at least 4 years, or at least 6 years of storage. The storage temperature can be about 21° C., about 20-25° C., or about 15-30° C.

Another degradation product of solid form quercetin compositions is 2-(3,4-dihydroxybenzoyloxy)-4,6-dihydroxybenzoic acid (DB-DBA). This byproduct was not predicted by prior studies of quercetin degradation in solution (Wang et al., 2016).

Consequently, provided herein are methods for detecting and measuring the level of DB-DBA in quercetin compositions. Also provided are methods to determine the safety of a quercetin composition by measuring the level of DB-DBA and comparing it to a threshold level. If the level of DB-DBA is above the threshold level, then the quercetin composition is deemed unsafe. If the level of DB-DBA is below the threshold level, then the quercetin composition is deemed not unsafe.

Methods to detect DB-DBA are known in the art, such as by liquid chromatography with UV detection. For example, a solution containing DB-DBA is subjected to liquid chromatography using gradient elution with the following conditions: stainless steel column with stationary phase endcapped octadecylsilyl silica for chromatography R; size (150×3.9) mm, particle size 5 microns. Mobile phase A: 0.1% phosphoric acid v/v; mobile phase B—methanol; column temperature: 25° C.; flow rate: 1 mL/min.; UV detection at 254 nm. Relative retention time is 1.00 for quercetin, and 0.77 for DB-DBA (FIG. 15). Content of DB-DBA relative to quercetin can be calculated by formula (in percentage):

$$X_i = \frac{S_i}{S_0},$$

where $S_i$—peak area of DB-DBA on the chromatogram of test solution;

$S_0$—peak area of quercetin on the chromatogram reference solution (a).

Applicant is unaware of prior studies regarding the toxic effect of DB-DBA, but a close homolog, digallic acid (DGA), is toxic to a range of human cells. DGA causes apoptosis in human lymphoblastoid cell lines (Bhouri et al., 2012a), and cytotoxicity in other human cell lines (Salem et al., 2011). DGA causes DNA fragmentation in the human lymphoblastoid cell line K562, a hallmark of apoptotic cell death, at concentrations of 200-800 microgram/ml (Bhouri et al., 2012b). DGA causes DNA fragmentation, caspase-3/8 activation and PARP cleavage (other hallmarks of apoptosis) at concentrations of 2.5-10 microgram/ml in human lymphoblastoid TK6 cells. DGA exhibits an $IC_{50}$ of 8.5 microgram/ml as measured by MTT assay (Bhouri et al., 2012a). The $IC_{50}$ of DGA by 72-hr MTT assay ranges from 7.3 to 86 microgram/ml in solid human tumor cell lines of different origin (92.1, OCM3, U-87MG, SK-MEL-28, and SK-OV-3). The lowest $IC_{50}$ of DGA was to melanoma OCM3 cells. DGA is also cytototoxic (with $IC_{50}$ 47 microgram/mil) to a normal cell line, retinal pigmented epithelial cells (ARPE-19) (Salem et al., 2011). DB-DBA differs from DGA by an additional hydroxyl group (marked) in DGA (see scheme below).

The chemical formula of DB-DBA differs from DGA by an additional hydroxyl group (underlined) in DGA (see scheme below).

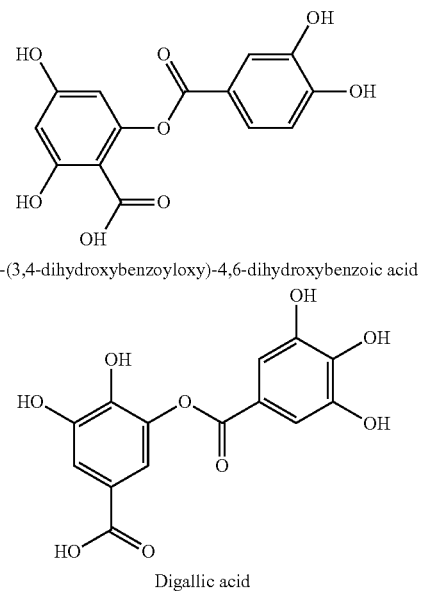

2-(3,4-dihydroxybenzoyloxy)-4,6-dihydroxybenzoic acid

Digallic acid

Shown herein is the toxic effect of DB-DBA in a cell viability assay. See Example 10.

In some embodiments, the solid form quercetin composition comprises less than 1% DB-DBA after 24 months at 20-25° C. In some embodiments, the solid form quercetin composition comprises less than 1% DB-DBA after 24 months at about 21° C. In some embodiments, the solid form quercetin composition comprises less than 0.6%, less than 0.7%, less than 0.8%, or less than 0.9% DB-DBA after 24 months at about 20-25° C. In some embodiments, the solid form quercetin composition comprises less than 0.6%, less than 0.7%, less than 0.8%, less than 0.9% DB-DBA after 24 months at about 21° C. In some embodiments, the solid form quercetin composition comprises less than 0.5% DB-DBA after 24 months at 20-25° C. In some embodiments, the solid form quercetin composition comprises less than 0.5% DB-DBA after 24 months at about 21° C.

Reduction of degradation product of solid form quercetin compositions stored in an inert gas atmosphere results in lowered formation of DB-DBA (see Example 14).

Methods to detect DB-DBA are known in the art, such as by liquid chromatography with UV detection. For example, a solution containing DB-DBA is subjected to liquid chromatography using gradient elution with the following conditions: stainless steel column with stationary phase endcapped octadecylsilyl silica for chromatography R; size (150×3.9) mm, particle size 5 microns. Mobile phase A: 0.1% phosphoric acid v/v; mobile phase B—methanol; column temperature: 25° C.; flow rate: 1 mL/min.; UV detection at 254 nm. Relative retention time is 1.00 for quercetin, and 0.77 for DB-DBA (FIG. 15). Content of DB-DBA relative to quercetin can be calculated by formula (in percentage):

$$X_i = \frac{S_i}{S_0},$$

where: $S_i$—peak area of DB-DBA on the chromatogram of test solution;
$S_0$—peak area of quercetin on the chromatogram reference solution (a).

In some embodiments, the quercetin composition is identified as unsafe if the level of DB-DBA is above about 0.54% of quercetin (w/w). In some embodiments, the quercetin composition is identified as not unsafe if the level of DB-DBA is below about 0.51±0.03%. In certain embodiments, the threshold level DB-DBA to determine a quercetin composition is unsafe/not unsafe is about 0.54%, about 0.53%, about 0.52%, about 0.51%, about 0.50%, about 0.49%, or about 0.48% (w/w) DB-DBA/quercetin. In certain embodiments, the threshold level DB-DBA to determine a quercetin composition is unsafe/not unsafe is about 2%, about 1.5%, about 1%, about 0.9%, about 0.8%, about 0.7% or about 0.6% (w/w) DB-DBA/quercetin.

In some embodiments, the solid form quercetin composition after 24 months at 20-25° C. has a 72 h-EC50 less than about 7.5 milligram/ml in a cytotoxicity assay with MDA-MB231 human breast cancer cells. In some embodiments, the solid form quercetin composition after 24 months at about 21° C. has a 72 h-EC50 less than about 7.5 milligram/ml in cytotoxicity assay with MDA-MB231 human breast cancer cells. In some embodiments, the solid form quercetin composition after 24 months at 20-25° C. has a 72 h-EC50 less than about 750 microgram/ml in a cytotoxicity assay with MDA-MB231 human breast cancer cells. In some embodiments, the solid form quercetin composition after 24 months at about 21° C. has a 72 h-EC50 less than about 750 microgram/ml in cytotoxicity assay with MDA-MB231 human breast cancer cells.

As noted above, one can observe toxicity of a quercetin composition that is contaminated by DB-DBA. Consequently, also provided herein are methods of assessing the safety of a quercetin composition by determining a 72 h-EC50 for the quercetin composition in a cytotoxicity assay with MDA-MB231 human breast cancer cells and comparing the 72 h-EC50 to a threshold level. The quercetin composition is identified as unsafe if the 72 h-EC50 is below the threshold level and not unsafe if the 72 h-EC50 is above the threshold level. In some embodiments the threshold level is about 7.5 milligram/ml and other embodiments the threshold level is about 750 microgram/ml.

Also provided are methods for reducing the rate of formation of DB-DBA by degradation of a solid form quercetin composition by (1) purging air from an airtight container containing the solid form quercetin composition and filling the container with an atmosphere consisting essentially of an inert gas or a combination of inert gases and (2) assessing the safety of the solid form quercetin composition according to methods described above. Assessing the safety of the solid form quercetin composition can be performed after storage of the solid form quercetin composition for a certain period of time. The assessment can be performed after at least one day, at least one week, at least one months, at least 3 months, at least six months, at least nine months, at least one year, at least 18 months, at least two years, at least 30 months, at least 3 years, at least 4 years, or at least 6 years of storage. The storage temperature can be about 21° C., about 20-25° C., about 15-30° C.

While not wishing to be held by theory, Applicant submits that a combination of the above toxic byproducts can additively contribute to the toxicity of a contaminated quercetin composition overall. Consequently, provided herein are methods of assessing safety of a quercetin composition by determining a level of at least two contaminants in the quercetin composition. In various embodiments, the contaminants can be two or more of protocatechuic acid, 2,4,6-trihydroxybenzoic acid, and 2-(3,4-dihydroxybenzoyloxy)-4,6-dihydroxybenzoic acid. The quercetin composition is identified as unsafe if the level of the at least two contaminants is above the threshold level. The quercetin composition is identified as not unsafe if the level of the at least two contaminants is below the threshold level. In some embodiments, the threshold level is 1 and calculated for the contaminants determined by the equation: T=(% (w/w) of protocatechuic acid/quercetin)/T1+(% (w/w) of 2,4,6-trihydroxybenzoic acid/quercetin)/T2+(% (w/w) of 2-(3,4-dihydroxybenzoyloxy)-4,6-dihydroxybenzoic acid/quercetin)/T3, wherein T1, T2, and T3 are the threshold level for safety for protocatechuic acid, 2,4,6-trihydroxybenzoic acid, and 2-(3,4-dihydroxybenzoyloxy)-4,6-dihydroxybenzoic acid, respectively. The threshold can be any threshold level for a contaminant as provided above. For a contaminant not selected to be determined, the contribution to the threshold level is zero.

In some embodiments, the threshold level is 1 and calculated for the contaminants determined by the equation: T=(% (w/w) of protocatechuic acid/quercetin)/0.65+(% (w/w) of 2,4,6-trihydroxybenzoic acid/quercetin)/0.33+(% (w/w) of 2-(3,4-dihydroxybenzoyloxy)-4,6-dihydroxybenzoic acid/quercetin)/2.6. For a contaminant not selected to be determined, the contribution to the threshold level is zero. For example, if the level determined of protocatechuic acid and 2,4,6-trihydroxybenzoic acid were 0.65% (w/w) and 0.07% (w/w) quercetin, respectively, then the threshold level of the combined contaminants is T=0.65/0.65+0.07/0.33+0/2.6=1+0.21+0=1.21. Because 1.21 is greater than 1, the quercetin composition would be identified as unsafe. As another example, if the level determined of protocatechuic acid, 2,4,6-trihydroxybenzoic acid, and 2-(3,4-dihydroxybenzoyloxy)-4,6-dihydroxybenzoic acid were 0.12% (w/w), 0.05% (w/w), and 0.51% (w/w) quercetin, respectively, then the threshold level of the combined contaminants is T=0.12/0.65+0.05/0.33+0.51/2.6=0.18+0.15+0.22=0.55. Because 0.55 is less than 1, the quercetin composition would be identified as not unsafe.

EMBODIMENTS

A1. A method of assessing safety of a quercetin composition comprising:
determining a level of a contaminant in the quercetin composition, wherein the contaminant comprises protocatechuic acid;
comparing the level of protocatechuic acid to a threshold level;

wherein the quercetin composition is identified as unsafe if the level of protocatechuic acid is above the threshold level; and, wherein the quercetin composition is identified as not unsafe if the level of protocatechuic acid is below the threshold level.

A2. The method of embodiment A1, wherein the threshold level is about 0.6%, about 0.5%, about 0.4%, about 0.3%, or about 0.2% (w/w) of protocatechuic acid/quercetin.

A3. The method of embodiment A1, wherein the threshold level is about 0.14%, about 0.13%, about 0.12%, about 0.11%, or about 0.10% (w/w) of protocatechuic acid/quercetin.

A4. The method of embodiment A1, wherein the threshold level is about 0.12±0.02% (w/w) of protocatechuic acid/quercetin.

A5. A method for reducing the rate of formation of protocatechuic acid by degradation of a solid form quercetin composition comprising (1) purging air from an airtight container containing the solid form quercetin composition and filling the container with an atmosphere consisting essentially of an inert gas or a combination of inert gases and (2) assessing the safety of the solid form quercetin composition according to any of the methods of embodiments A1 to A4.

A6. A method of assessing safety of a quercetin composition comprising:
determining a level of a contaminant in the quercetin composition, wherein the contaminant comprises 2,4,6-trihydroxybenzoic acid;
comparing the level of 2,4,6-trihydroxybenzoic acid to a threshold level;
wherein the quercetin composition is identified as unsafe if the level of 2,4,6-trihydroxybenzoic acid is above the threshold level; and,
wherein the quercetin composition is identified as not unsafe if the level of 2,4,6-trihydroxybenzoic acid is below the threshold level.

A7. The method of embodiment A6, wherein the threshold level is about 0.17%, about 0.16%, about 0.15%, about 0.14%, about 0.13%, about 0.12%, about 0.11%, about 0.10%, about 0.09%, or about 0.08% (w/w) of 2,4,6-trihydroxybenzoic acid/quercetin.

A8. The method of embodiment A6, wherein the threshold level is about 0.07%, about 0.06%, about 0.05%, about 0.04%, or about 0.03% (w/w) of 2,4,6-trihydroxybenzoic acid/quercetin.

A9. The method of embodiment A6, wherein the threshold level is about 0.05±0.02% (w/w) of 2,4,6-trihydroxybenzoic acid/quercetin.

A10. A method for reducing the rate of formation of 2,4,6-trihydroxybenzoic acid by degradation of a solid form quercetin composition comprising (1) purging air from an airtight container containing the solid form quercetin composition and filling the container with an atmosphere consisting essentially of an inert gas or a combination of inert gases and (2) assessing the safety of the solid form quercetin composition according to any of the methods of embodiments A6 to A9.

A11. A method of assessing safety of a quercetin composition comprising:
determining a level of a contaminant in the quercetin composition, wherein the contaminant comprises 2-(3,4-dihydroxybenzoyloxy)-4,6-dihydroxybenzoic acid;
comparing the level of 2-(3,4-dihydroxybenzoyloxy)-4,6-dihydroxybenzoic acid to a threshold level;
wherein the quercetin composition is identified as unsafe if the level of 2-(3,4-dihydroxybenzoyloxy)-4,6-dihydroxybenzoic acid is above the threshold level; and,
wherein the quercetin composition is identified as not unsafe if the level of 2-(3,4-dihydroxybenzoyloxy)-4,6-dihydroxybenzoic acid is below the threshold level.

A12. The method of embodiment A11, wherein the threshold level is about 2%, about 1.5%, about 1%, about 0.9%, about 0.8%, about 0.7% or about 0.6% (w/w) of 2-(3,4-dihydroxybenzoyloxy)-4,6-dihydroxybenzoic acid/quercetin.

A13. The method of embodiment A11, wherein the threshold level is about 0.54%, about 0.53%, about 0.52%, about 0.51%, about 0.50%, about 0.49%, or about 0.48% (w/w) of 2-(3,4-dihydroxybenzoyloxy)-4,6-dihydroxybenzoic acid/quercetin.

A14. The method of embodiment A11, wherein the threshold level is about 0.51±0.03% (w/w) of 2-(3,4-dihydroxybenzoyloxy)-4,6-dihydroxybenzoic acid/quercetin.

A15. A method for reducing the rate of formation of 2-(3,4-dihydroxybenzoyloxy)-4,6-dihydroxybenzoic acid by degradation of a solid form quercetin composition comprising (1) purging air from an airtight container containing the solid form quercetin composition and filling the container with an atmosphere consisting essentially of an inert gas or a combination of inert gases and (2) assessing the safety of the solid form quercetin composition according to any of the methods of embodiments A11 to A14.

A16. A method of assessing safety of a quercetin composition comprising:
determining a level of a contaminant in the quercetin composition, wherein the contaminant is selected from the group consisting of: protocatechuic acid, 2,4,6-trihydroxybenzoic acid, and 2-(3,4-dihydroxybenzoyloxy)-4,6-dihydroxybenzoic acid comparing the level of contaminant to a threshold level;
wherein the quercetin composition is identified as unsafe if the level of contaminant is above the threshold level; and,
wherein the quercetin composition is identified as not unsafe if the level of contaminant is below the threshold level.

A17. The method of embodiment A16, wherein the contaminant is protocatechuic acid and the threshold level is about 0.6%, about 0.5%, about 0.4%, about 0.3%, or about 0.2% (w/w) of protocatechuic acid/quercetin.

A18. The method of embodiment A16, wherein the contaminant is protocatechuic acid and the threshold level is about 0.14%, about 0.13%, about 0.12%, about 0.11%, or about 0.10% (w/w) of protocatechuic acid/quercetin.

A19. The method of embodiment A16, wherein the contaminant is protocatechuic acid and the threshold level is about 0.12±0.02% (w/w) of protocatechuic acid/quercetin.

A20. The method of embodiment A16, wherein the contaminant is 2,4,6-trihydroxybenzoic acid and the threshold level is about 0.17%, about 0.16%, about 0.15%, about 0.14%, about 0.13%, about 0.12%, about 0.11%, about 0.10%, about 0.09%, or about 0.08% (w/w) 2,4,6-THBA/quercetin.

A21. The method of embodiment A16, wherein the contaminant is 2,4,6-trihydroxybenzoic acid and the threshold level is about 0.07%, about 0.06%, about 0.05%, about 0.04%, about 0.03% (w/w) of 2,4,6-trihydroxybenzoic acid/quercetin.

A22. The method of embodiment A16, wherein the contaminant is 2,4,6-trihydroxybenzoic acid and the threshold level is about 0.05±0.02% (w/w) of 2,4,6-trihydroxybenzoic acid/quercetin.

A23. The method of embodiment A16, wherein the contaminant is 2-(3,4-dihydroxybenzoyloxy)-4,6-dihydroxybenzoic acid and the threshold level of 2-(3,4-dihydroxybenzoyloxy)-4,6-dihydroxybenzoic acid is about 2%, about 1.5%, about 1%, about 0.9%, about 0.8%, about 0.7% or about 0.6% (w/w) of 2-(3,4-dihydroxybenzoyloxy)-4,6-dihydroxybenzoic acid/quercetin.

A24. The method of embodiment A16, wherein the contaminant is 2-(3,4-dihydroxybenzoyloxy)-4,6-dihydroxybenzoic acid and the threshold level is about 0.54%, about 0.53%, about 0.52%, about 0.51%, about 0.50%, about 0.49%, or about 0.48% (w/w) of 2-(3,4-dihydroxybenzoyloxy)-4,6-dihydroxybenzoic acid/quercetin.

A25. The method of embodiment A16, wherein the contaminant is 2-(3,4-dihydroxybenzoyloxy)-4,6-dihydroxybenzoic acid and the threshold level is about 0.51±0.03% (w/w) of 2-(3,4-dihydroxybenzoyloxy)-4,6-dihydroxybenzoic acid/quercetin.

A26. A method of assessing safety of a quercetin composition comprising:
determining a level of at least two contaminants in the quercetin composition, wherein the contaminants are selected from the group consisting of: protocatechuic acid, 2,4,6-trihydroxybenzoic acid, and 2-(3,4-dihydroxybenzoyloxy)-4,6-dihydroxybenzoic acid comparing the level of the at least two contaminants in combination to a threshold level;
wherein the quercetin composition is identified as unsafe if the level of the at least two contaminants in combination is above the threshold level; and,
wherein the quercetin composition is identified as not unsafe if the level of the at least two contaminants in combination is below the threshold level.

A27. The method of embodiment A26, wherein the threshold level is 1 and calculated for the contaminants determined by the equation: (% (w/w) of protocatechuic acid/quercetin)/T1+(% (w/w) of 2,4,6-trihydroxybenzoic acid/quercetin)/T2+(% (w/w) of 2-(3,4-dihydroxybenzoyloxy)-4,6-dihydroxybenzoic acid/quercetin)/T3;
wherein T1 is the threshold level of protocatechuic acid, T2 is the threshold level of 2,4,6-trihydroxybenzoic acid, and T3 is the threshold level of 2-(3,4-dihydroxybenzoyloxy)-4,6-dihydroxybenzoic acid/quercetin; and,
wherein for a contaminant not selected to be determined, the contribution to the threshold level is zero.

A28. The method of embodiment A26, wherein the threshold level is 1 and calculated for the contaminants determined by the equation: (% (w/w) of protocatechuic acid/quercetin)/0.65+(% (w/w) of 2,4,6-trihydroxybenzoic acid/quercetin)/0.33+(% (w/w) of 2-(3,4-dihydroxybenzoyloxy)-4,6-dihydroxybenzoic acid/quercetin)/2.6;
wherein for a contaminant not selected to be determined, the contribution to the threshold level is zero.

A29. A method for reducing the rate of formation of protocatechuic acid, 2,4,6-trihydroxybenzoic acid, or 2-(3,4-dihydroxybenzoyloxy)-4,6-dihydroxybenzoic acid by degradation of a solid form quercetin composition comprising (1) purging air from an airtight container containing the solid form quercetin composition and filling the container with an atmosphere consisting essentially of an inert gas or a combination of inert gases and (2) assessing the safety of the solid form quercetin composition according to any of the methods of embodiments A16 to A28.

A30. The method of any of embodiments A1 to A29, wherein the quercetin composition comprises a pharmaceutically acceptable composition.

A31. The method of any of embodiments A1 to A30, wherein the quercetin composition comprises a solid form quercetin composition.

A32. The method of embodiment A31, wherein the solid form quercetin composition comprises freeze-dried quercetin.

A33. The method of embodiment A31, wherein the solid form quercetin composition is prepared by spray drying, rotoevaporation, or crystallization.

A34. The method of any of embodiments A1 to A33, wherein the quercetin composition further comprises a drug delivery formulation.

A35. The method of embodiment A34, wherein the drug delivery formulation is selected from the group consisting of: a lipid-based carrier, a polymer-based carrier, nanoparticles, inclusion complexes, micelles, and a conjugate-based capsulation.

A36. The method of embodiment A35, wherein the drug delivery formulation comprises a lipid-based carrier and the lipid-based carrier is selected from the group consisting of: glycerin, propylene glycol, stearate, and olive oil.

A37. The method of embodiment A35, wherein the drug delivery formulation comprises a polymer-based carrier and the polymer-based carrier comprises polyvinylpyrrolidone.

A38. The method of embodiment A37, wherein the quercetin composition comprises about 8:1, about 9:1, about 10:1, about 11:1, or about 12:1 polyvinylpyrrolidone:quercetin w/w.

A39. The method of embodiment A37, wherein the quercetin composition comprises 7-11% quercetin and 89-93% polyvinylpyrrolidone w/w.

A40. The method of any of embodiments A1 to A39, wherein determining the level of a contaminant in the quercetin composition comprises chromatography.

A41. The method of embodiment A40, wherein the chromatography is selected from the group consisting of: liquid chromatography, thin layer chromatography, gas chromatography, and electrophoresis.

A42. The method of embodiment A41 wherein liquid chromatography comprises high-performance (HPLC) or ultra performance (UPLC) liquid chromatography.

A43. The method of any of embodiments A40 to A42 further comprising ultraviolet, diode-array, mass, evaporating light scattering, conductometric, electrochemical, or fluorescence detection.

A44. The method of embodiment A41, wherein the chromatography is gas chromatography and further comprises flame-ionizing or mass detection.

B1. A method of assessing safety of a quercetin composition comprising:
determining a 48 h-EC50 for the quercetin composition in a *Daphnia magna* mobility assay; comparing the 48 h-EC50 to a threshold level;
wherein the quercetin composition is identified as unsafe if the 48 h-EC50 is below the threshold level;
wherein the quercetin composition is identified as not unsafe if the 48 h-EC50 is above the threshold level; and,
wherein the threshold level is about 1 mg/L.

B2. A method of assessing safety of a quercetin composition comprising:
determining a 48 h-EC50 for the quercetin composition in a *Daphnia magna* mobility assay;
comparing the 48 h-EC50 to a threshold level;
wherein the quercetin composition is identified as unsafe if the 48 h-EC50 is below the threshold level;
wherein the quercetin composition is identified as not unsafe if the 48 h-EC50 is above the threshold level; and, wherein the threshold level is about 0.5 mg/L.

B3. A method of assessing safety of a quercetin composition comprising:
determining a 72 h-EC50 in a cytotoxicity assay using MDA-MB231 human breast cancer cells; comparing the 72 h-EC50 to a threshold level;
wherein the quercetin composition is identified as unsafe if the 72 h-EC50 is below the threshold level;
wherein the quercetin composition is identified as not unsafe if the 72 h-EC50 is above the threshold level; and, wherein the threshold level is about 7.5 mg/ml.

B4. A method of assessing safety of a quercetin composition comprising:
determining a 72 h-EC50 in a cytotoxicity assay using MDA-MB231 human breast cancer cells;
comparing the 72 h-EC50 to a threshold level;
wherein the quercetin composition is identified as unsafe if the 72 h-EC50 is below the threshold level;
wherein the quercetin composition is identified as not unsafe if the 72 h-EC50 is above the threshold level; and,
wherein the threshold level is about 750 micrograms/ml.

B5. The method of any of embodiments B1 to B4, wherein the quercetin composition comprises a pharmaceutically acceptable composition.

B6. The method of any of embodiments B1 to B5, wherein the quercetin composition comprises a solid form quercetin composition.

B7. The method of embodiment B6, wherein the solid form quercetin composition comprises freeze-dried quercetin.

B8. The method of embodiment B6, wherein the solid form quercetin composition is prepared by spray drying, rotoevaporation, or crystallization.

B9. The method of any of embodiments B1 to B8, wherein the quercetin composition further comprises a drug delivery formulation.

B10. The method of embodiment B9, wherein the drug delivery formulation is selected from the group consisting of: a lipid-based carrier, a polymer-based carrier, nanoparticles, inclusion complexes, micelles, and a conjugate-based capsulation.

B11. The method of embodiment B10, wherein the drug delivery formulation comprises a lipid-based carrier and the lipid-based carrier is selected from the group consisting of: glycerin, propylene glycol, stearate, and olive oil.

B12. The method of embodiment B10, wherein the drug delivery formulation comprises a polymer-based carrier and the polymer-based carrier comprises polyvinylpyrrolidone.

B13. The method of embodiment B12, wherein the quercetin composition comprises about 8:1, about 9:1, about 10:1, about 11:1, or about 12:1 polyvinylpyrrolidone:quercetin w/w.

B14. The method of embodiment B12, wherein the quercetin composition comprises 7-11% quercetin and 89-93% polyvinylpyrrolidone w/w.

REFERENCES

Bhouri, W., J. Boubaker, I. Skandrani, K. Ghedira, and L. Chekir Ghedira. 2012a. Investigation of the apoptotic way induced by digallic acid in human lymphoblastoid TK6 cells. *Cancer Cell International*. 12:26.

Bhouri, W., I. Skandrani, Mt. Sghair, M.-G. D. Franca, K. Ghedira, and L. C. Ghedira. 2012b. Digallic acid from Pistascia lentiscus fruits induces apoptosis and enhances antioxidant activities. *Phytotherapy Research*. 26:387-391.

Dachineni, R., D. R. Kumar, E. Callegari, S. S. Kesharwani, R. Sankaranarayanan, T. Seefeldt, H. Tummala, and G. J. Bhat. 2017. Salicylic acid metabolites and derivatives inhibit CDK activity: Novel insights into aspirin's chemopreventive effects against colorectal cancer. *International Journal of Oncology*. 51:1661-1673.

Denina, R. 2013. Heart Failure Treatment In Patients With RecurrentMyocardial Infarction. *The Pharma Innovation*. 2:30-35.

Graefe, E., W. Joerg, M. Silke, R. Anne-Kathrin, U. Bernhard, D. Bernd, P. Holger, J. Gisela, D. Hartmut, and V. Markus. 2001. Pharmacokinetics and Bioavailability of Quercetin Glycosides in Humans. *The Journal of Clinical Pharmacology*. 41:492-499.

Harwood, M., B. Danielewska-Nikiel, J. F. Borzelleca, G. W. Flamm, G. M. Williams, and T. C. Lines. 2007. A critical review of the data related to the safety of quercetin and lack of evidence of in vivo toxicity, including lack of genotoxic/carcinogenic properties. *Food and Chemical Toxicology*. 45:2179-2205.

Kamaya, Y., Y. Fukaya, and K. Suzuki. 2005. Acute toxicity of benzoic acids to the crustacean *Daphnia magna*. *Chemosphere*. 59:255-261.

Kuzmenko, M. A., V. B. Pavlyuchenko, L. V. Tumanovskaya, V. E. Dosenko, and A. A. Moybenko. 2013. [Experimental therapy of cardiac remodeling with quercetin-containing drugs]. *Patol Fiziol Eksp Ter*: 17-22.

Martins, J., L. Oliva Teles, and V. Vasconcelos. 2007. Assays with *Daphnia magna* and *Danio rerio* as alert systems in aquatic toxicology. *Environment International*. 33:414-425.

Nakamura, Y., K. Torikai, and H. Ohigashi. 2001. Toxic Dose of a Simple Phenolic Antioxidant, Protocatechuic Acid, Attenuates the Glutathione Level in ICR Mouse Liver and Kidney. *Journal of Agricultural and Food Chemistry*. 49:5674-5678, Pashevin, D. A., L. V. Tumanovska, V. E. Dosenko, V. S. Nagibin, V. L. Gurianova, and A. A. Moibenko. 2011. Antiatherogenic effect of quercetin is mediated by proteasome inhibition in the aorta and circulating leukocytes. *Pharmacol Rep*. 63:1009-18.

Porcu, E. P., M. Cossu, G. Rassu, P. Giunchedi, G. Cerri, J. Pourová, I. Najmanová, T. Migkos, V. Pilařová, L. Nováková, P. Mladěnka, and E. Gavini. 2018. Aqueous injection of quercetin: An approach for confirmation of its direct in vivo cardiovascular effects. *International Journal of Pharmaceutics*. 541:224-233.

Roos, C. M., B. Zhang, A. K. Palmer, M. B. Ogrodnik, T. Pirtskhalava, N. M. Thalji, M. Hagler, D. Jurk, L. A. Smith, G. Casaclang-Verzosa, Y. Zhu, M. J. Schafer, T. Tchkonia, J. L. Kirkland, and J. D. Miller. 2016. Chronic senolytic treatment alleviates established vasomotor dysfunction in aged or atherosclerotic mice. *Aging Cell*. 15:973-977.

Ryzhkova, N. O., T. I. Gavrilenko, and O. M. Parkhomenko. 2016. Korvitin Reduces the High Maintenance of Myeloperoxidase in Plasma of Blood of Patients with the Acute Infarct of Myocardium. *Fiziol Zh*. 62:87-93.

Salem, M. M., F. H. Davidoff, and M. N. Abdel-Rahman. 2011. In vitro anti-uveal melanoma activity of phenolic compounds from the Egyptian medicinal plant Acacia nilotica. *Fitoterapia*. 82:1279-1284.

Straub, J. O. 2002. Environmental risk assessment for new human pharmaceuticals in the European Union according to the draft guideline/discussion paper of January 2001. *Toxicology Letters*. 131:137-143.

Wang, W., C. Sun, L. Mao, P. Ma, F. Liu, J. Yang, and Y. Gao. 2016. The biological activities, chemical stability, metabolism and delivery systems of quercetin: A review. *Trends in Food Science & Technology.* 56:21-38.

Xie, Z., Z. Guo, Y. Wang, J. Lei, and J. Yu. 2018. Protocatechuic acid inhibits the growth of ovarian cancer cells by inducing apoptosis and autophagy. *Phytotherapy Research.* 0.

Xu, M., T. Pirtskhalava, J. N. Farr, B. M. Weigand, A. K. Palmer, M. M. Weivoda, C. L. Inman, M. B. Ogrodnik, C. M. Hachfeld, D. G. Fraser, J. L. Onken, K. O. Johnson, G. C. Verzosa, L. G. P. Langhi, M. Weigl, N. Giorgadze, N. K. LeBrasseur, J. D. Miller, D. Jurk, R. J. Singh, D. B. Allison, K. Ejima, G. B. Hubbard, Y. Ikeno, H. Cubro, V. D. Garovic, X. Hou, S. J. Weroha, P. D. Robbins, L. J. Niedernhofer, S. Khosla, T. Tchkonia, and J. L. Kirkland. 2018. Senolytics improve physical function and increase lifespan in old age. *Nature Medicine.* 24:1246-1256.

Yin, M.-C., C.-C. Lin, H.-C. Wu, S.-M. Tsao, and C.-K. Hsu. 2009. Apoptotic Effects of Protocatechuic Acid in Human Breast, Lung, Liver, Cervix, and Prostate Cancer Cells: Potential Mechanisms of Action. *Journal of Agricultural and Food Chemistry.* 57:6468-6473.

EXAMPLES

Example 1

A Solid Form Quercetin Composition in an Air Atmosphere Undergoes Degradation in Ambient Temperature Storage Preparation of Lyophilized 90%/10% PVP/Quercetin Preparation of Intermediate Product Solution Preparation of alcohol solution (dissolution of quercetin and polyvinylpyrrolidone (PVP) in ethanol) and its evaporation (the formation of a homogeneous dry basis) were carried out with a rotary evaporator (Strike 5000, Steroglass, Perugia, Italy). 25 L Ethanol 96% (high-purity solvent, SE "Ukrspirt", Lipniki, Ukraine), 1.0 kg quercetin (high-purity solvent, SE "Ukrspirt", Lipniki, Ukraine) and 9.01 kg polyvinylpyrrolidone (PVP) (EP grade, BASF SE, Ludwigshafen, Germany) were loaded into a 100 liter round-bottomed flask of the rotary evaporator. Dissolution was performed using the following parameters:

| | |
|---|---|
| Temperature of water-bath | (70 ± 5)° C. |
| Vacuum level | 800 mbar |
| Rate of stirring | 50-100 rpm |
| Duration | 3.0 hours |

Stirring continued until the components were completely dissolved (visual control).

Evaporation of alcohol solution (obtaining of dry basis). Upon dissolution, the vacuum level was gradually increased at such a rate to maintain boiling of the solution. According to evaporation of solution the speed of rotation of flask was reduced. The evaporation continued until dryness.

| | |
|---|---|
| Temperature of water-bath | (70 ± 5)° C. |
| Vacuum level at the beginning of evaporation | 800 mbar |
| Vacuum level at the end of evaporation | 24-26 mbar |
| Rate of stirring | 50-100 rpm |
| Duration of evaporation | (7.0-7.5) hours |

A sodium hydroxide solution was prepared by charging a reactor (PCBF100, OLSA, Milan, Italy) with 13.5 L water for injection and 41.5 g sodium hydroxide (pharma grade EP, SPOLCHEMIE, Czech Republic) and stirred until complete dissolution. The rotational speed of the mixer was 295-300 rpm and the dissolution time was approximately 5 minutes.

Preparation of Aqueous Solution

The dry basis, (obtained at the stage of evaporation of alcohol solution), was dissolved in 52.0 L water for injection. After dissolution of the mass, a reactor (TK001 PCBF50, OLSA, Milan, Italy) was charged with the sodium hydroxide solution using a peristaltic pump (MASTER-FLEX LS 77301-20, MASTER-FLEX, Vernon Hills, USA) to adjust the pH of the solution to about 6.7-7.2. The resulting intermediate product solution was prefiltered using a cartridge filter with a pore size of 0.20 micron (DA36MDMM002MCY2, DANMIL NS, Greve, Denmark).

Filling of the Vials

The intermediate product solution was tested for microbial load on a filter pursuant to standard methods.

Glass vials (cat #0111075.1063, Medical Glass, Bratislava, Slovak Republic) were filled with a solution of the intermediate product on a filling and capping machine using a sterile filter-capsule with 0.45 and 0.22 micron pore size (SARTOBRAN P, Sartorius Stedim Biotech GmbH, Gottingen, Germany).

The volume of filled intermediate product solution was approximately 3.6-4.2 ml. The filled vials were topped with rubber stoppers (cat #C5919, Aptar Stelmi SAS, Granville, France) in vented position. The vials were transferred to a transport laminar trolley (LF 0.6×0.9, CHRIST, Osterode am Harz, Germany) and passed to the lyophilyzation process.

Lyophilyzation (Sublimation) of the Intermediate Product Solution

Drying of the intermediate product solution was performed in a lyophilizer (EPSILON 2-45 DS, CHRIST, Osterode am Harz, Germany) according to manufacturer instruction. After lyophilization, the vials were removed from the lyophilizer, and then the rubber stoppers tightly closed.

Sealing (Packing) of Vials

The stoppered vials were capped with aluminum caps (cat #K-2-20, Chernivets'kyy Zavod Medychnykh Vyrobiv, Chernivtsi, Ukraine) on a filling and capping machine. Sealing (packing), the hermeticity, and the quality of the lyophilized product were tested in accordance with QC procedures.

Packaging and Labeling

Vial labeling was performed on a labeling machine.

Labeled vials were placed manually into a cassette, 5 vials per cassette. Each cassette together with instruction for medical use was put into a case.

Cases were placed into boxes together with the label "Packer". The box was covered with adhesive tape (with a logo). A group label printed with the batch number and expiration date was glued with a transparent tape Example 2

A Solid Form Quercetin Composition in an Air Atmosphere Undergoes Degradation in Ambient Temperature Storage Vials of CORVITIN®, a medical formulation of quercetin (10%)/PVP (90%) wherein the solid form quercetin composition is in an air atmosphere, were stored at room temperature (21° C.) and samples were taken at indicated time points (0, 6, 12, 18, 24 and 36 months).

Test solution. 400.0 mg of vial contents was dissolved in 100 ml 96% (v/v) ethanol. 2.0 ml of the solution was diluted with 96% (v/v) ethanol to 100.0 ml.

Reference solution. 40.0 mg of working standard of quercetin (assay: 97.5%-101.5%, PJSC SIC "Borshchahivskiy CPP", Kiev, Ukraine) was dissolved in 100 ml 96% (v/v) ethanol. Then 2.0 ml of the solution was diluted to 100.0 ml with 96% (v/v) ethanol.

The absorbance of the test solution and of the reference solution was measured using the spectrophotometer at 374 nm and a 1-cm cuvette using 96% (v/v) ethanol as a blank solution.

Vial content of quercetin ($X_1$) was determined by the formula:

$$X_1 = \frac{A_1 * m_0 * 100 * 100 * 2 * b * P}{A_0 * m_1 * 100 * 2 * 100 * 100} = \frac{A_1 * m_0 * b * P}{A_0 * m_1 * 100},$$

where $A_1$—the absorbance of the test solution at 374 nm;
$A_0$—the absorbance of the reference solution at 374 nm;
$m_1$—the weight of the sample of the preparation, milligrams;
$m_0$—the weight of the sample of quercetin reference solution, milligrams;
b—the average vial contents, milligrams;
P—the content of quercetin in quercetin RS, percent.

Data from 3 independent experiments are shown in FIG. 1. Based on these experiments, quercetin content in CORVITIN® decreases gradually during storage at a rate of about 2.3% per 12 months.

Example 3

Formation of Byproducts of Solid Form Quercetin Degradation in Ambient Temperature Storage Vials of CORVITIN® were stored for 18 months at 20-25° C.

For test solution content of one vial with 70 ml of 96% ethanol was transferred to a 100 ml volumetric flask, diluted to 100 ml with the same solvent and mixed. For reference solution a, 1.0 ml of test solution was placed in a 100 ml volumetric flask, diluted to 100 ml with 96% ethanol and mixed. For reference solution b, 10.0 mg working standard of quercetin for system suitability (containing isorhamnetin and kaempferol, PJSC SIC "Borshchahivskiy CPP", Kiev, Ukraine) was dissolved in 30 ml of 96% ethanol, diluted to 50 ml with the same solvent and mixed. Chromatography was performed on a using a Dionex UltiMate 3000 HPLC system (Thermo Fisher Scientific, Inc., Waltham, Mass.) with DAD and MS detectors (3200 QTRAP System (AB Sciex LLC, Framingham, Mass.)) connected consecutively using gradient elution with the following conditions:

stainless steel column with stationary phase end-capped octadecylsilyl silica for chromatography; size (150×3.9) mm, particle size 5 microns
Mobile phase A: 1.0 mL of phosphoric acid diluted to 1000 mL with water for chromatography, mixed and degassed;
Mobile phase B: methanol gradient grade;
Column temperature: 25° C.
Flow rate: 1 mL/min.;
Detection at 254 nm;
injection volume: 10 microL.

Gradient Program:

| Time, min | Mobile phase A, % (V/V) | Mobile phase B, % (V/V) |
|---|---|---|
| 0 | 80 | 20 |
| 1 | 80 | 20 |
| 16 | 20 | 80 |
| 18 | 20 | 80 |
| 19 | 80 | 20 |
| 25 | 80 | 20 |

The chromatography system was deemed suitable if the following requirements are performed:
resolution: minimum 2.0 between the principal peak due to quercetin and the peak due to kaempferol.

Inject test solution and reference solution (a). Peaks of quercetin and kaempferol as references were determined by relative retention times of 1.00 and 1.11

Contaminants with retention times of 0.30, 0.34 and 0.77 were observed and are marked as PCA, 2,4,6-THBA and DB-DBA in FIG. 2.

Example 4

Identification of Products of Solid Form Quercetin Degradation in Ambient Temperature Storage As noted above, samples of CORVITIN® were analyzed by liquid chromatography using a Dionex UltiMate 3000 HPLC system (Thermo Fisher Scientific, Inc., Waltham, Mass.) with DAD and MS detectors (3200 QTRAP System (AB Sciex LLC, Framingham, Mass.)) connected consecutively. DAD and MS-detector. Ionization ESI and operating mode Q3 and EPI were used. Flavonols, such as quercetin, are easily deprotonated allowing for facile ionization and strong signals at trace amounts in the negative mode. Q3—full scan mode allows recording of the MS spectra in a given range (in this case, 50-1000 m/z) at each point of the chromatogram. It also allows establishing the m/z ratio for the molecular ion. EPI (Enhance Product Ion Scan) is used to obtain the mass of fragments formed during fragmentation of the molecular ion with a given m/z ratio. Linear Ion Trap (LIT) scan mode was used for accumulating fragments to obtain a MS spectra with high-intensity and high resolution.

Example 5

Figure 3A:
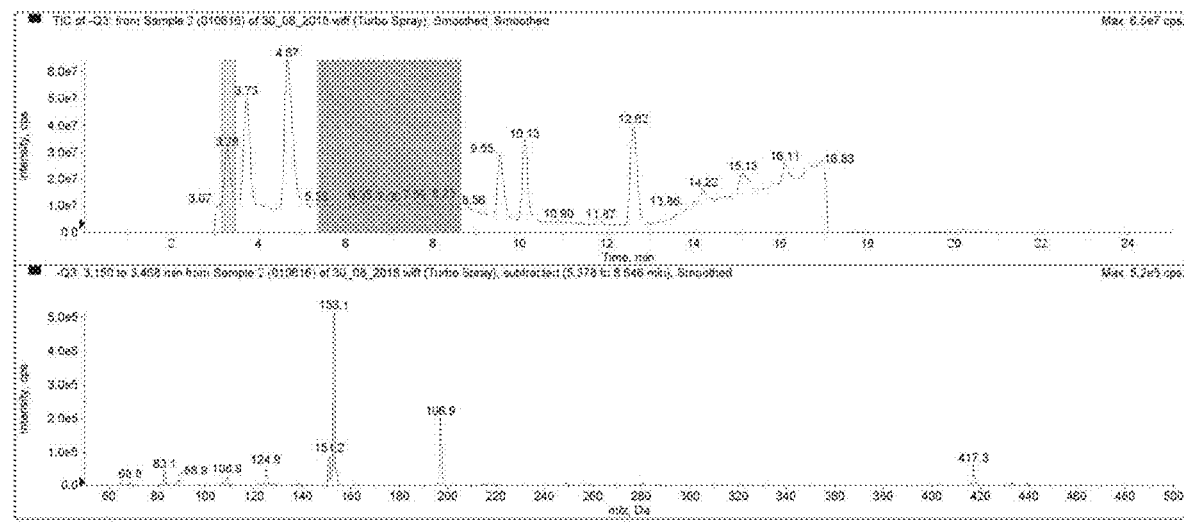
FIGS. 3A-3B show identification of protocatechuic acid by mass spectrometry.

Identification of Protocatechuic Acid as Byproduct of Solid Form Quercetin Degradation in Ambient Temperature Storage The MS spectrum of the peak with a retention time 3.93 min, (relative retention 0.30) of Example 4 is shown in FIG. 3A. On the chromatogram obtained from the test solution, the peak with a molecular ion mass m/z=153 was observed using Q3 mode.

Figure 3B:
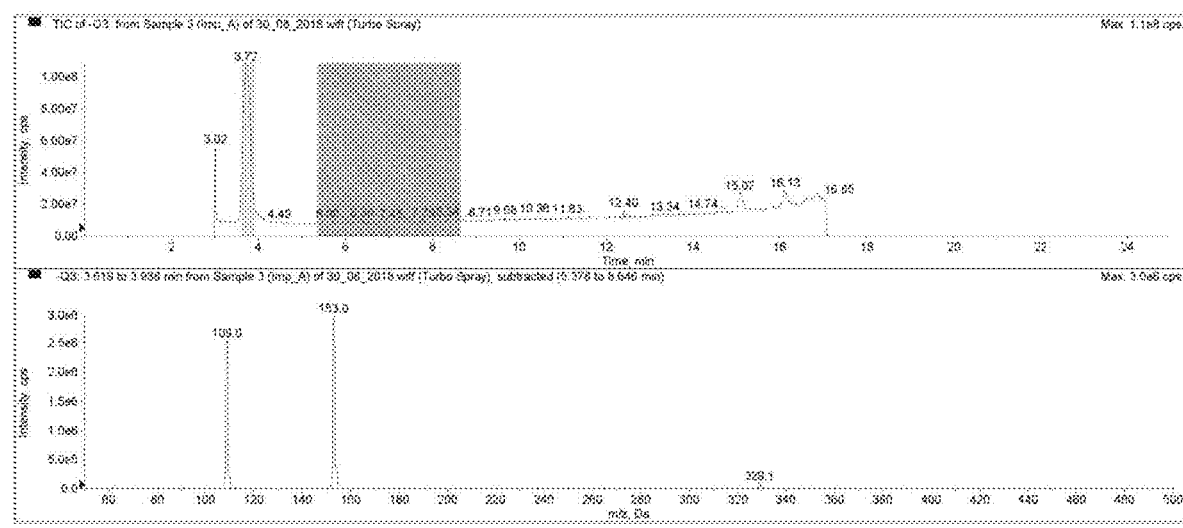

The fragmentation of the molecular ion m/z=153 was investigated using EPI mode, negative polarity, collision energy −10 V-30 V. Another peak with m/z=109 was also observed (FIG. 3B).

The MS spectra of fragmentation shows that the peak with a relative retention 0.30 corresponds to 3,4-dihydroxybenzoic acid (protocatechuic acid) (PCA in FIG. 2).

Figure 4:
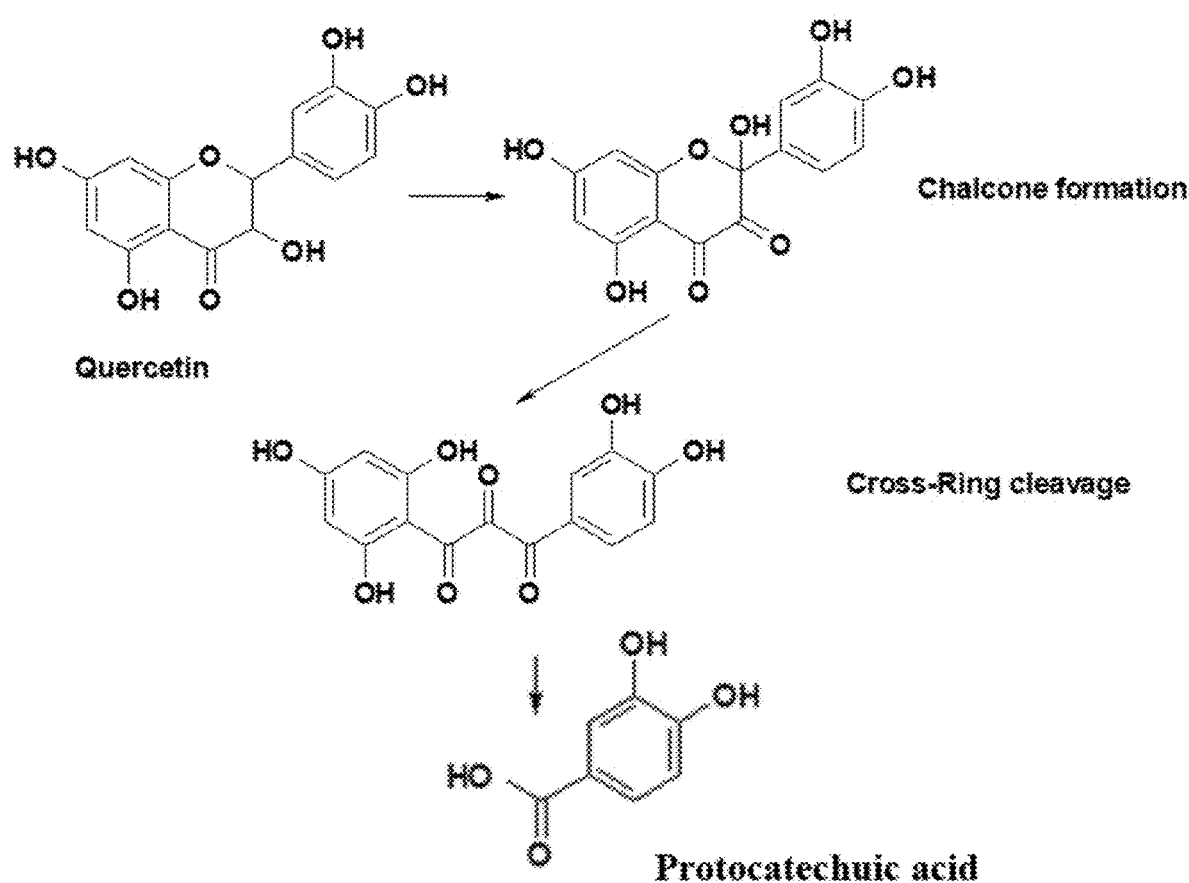
FIG. 4 shows a schema for the mechanism of formation of protocatechuic acid from quercetin.

This compound is a product of quercetin degradation through the formation of an intermediate product—chalcon. The proposed chemical mechanism of formation of protocatechuic acid is shown in FIG. 4.

FIG. 5 shows retention times, UV spectra and structures of protocatechuic acid and quercetin. protocatechuic acid has a relative retention time (RRT) 0.30, whereas RRT for quercetin is 1.0. Major absorption peaks of protocatechuic acid are 203.9, 216.3, and 260.2 nm, while those of quercetin are 203.7, 255.6 and 366 nm.

Figure 6:
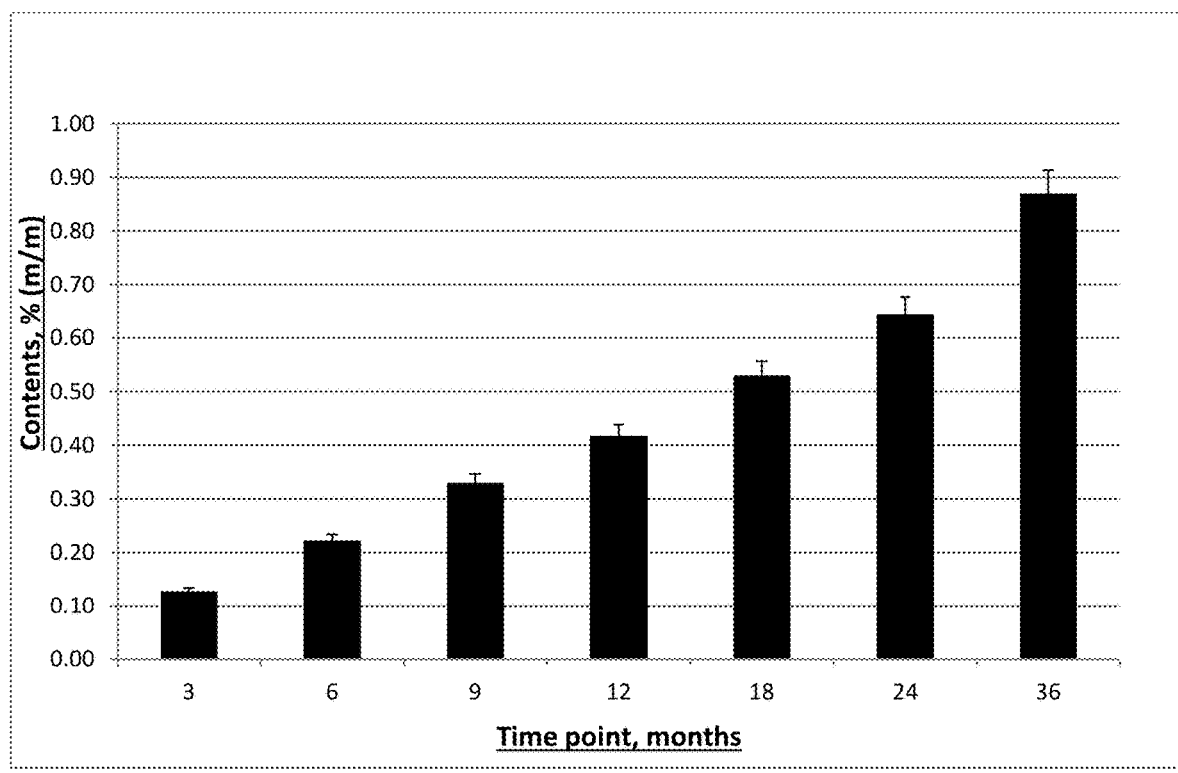
FIG. 6 shows time-dependent accumulation of protocatechuic acid of solid form quercetin composition in air atmosphere under ambient temperature conditions.

FIG. 6 shows the concomitant time-dependent accumulation of protocatechuic acid during quercetin degradation, increasing at each time point measured, from about 0.1% (w/w) protocatechuic acid/quercetin at 3 months storage to about 0.9% protocatechuic acid/quercetin at 36 months storage at 20-25° C.

Example 6

Figure 7:
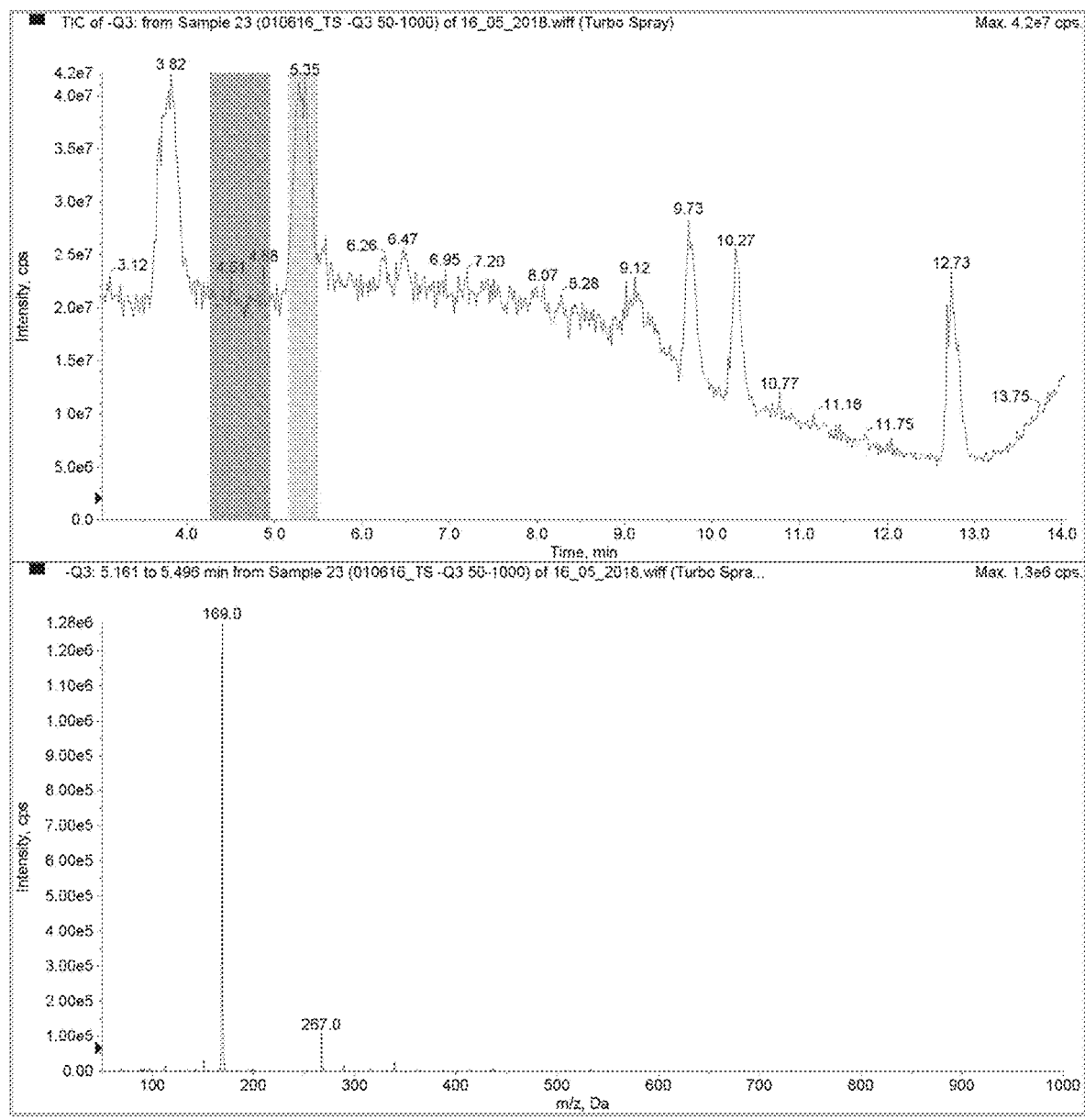
FIG. 7 shows HPLC-Mass Spectrometry results (LC (upper trace) and mass spectrum (lower trace)) of solid form quercetin stored for 18 months at 20-25° C. of a peak with a retention time 5.35 min, (relative retention 0.44) showing identification of 2,4,6-trihydroxybenzoic acid (2,4,6-THBA) by mass spectrometry.

Identification of 2,4,6-Trihydroxybenzoic Acid as Byproduct of Solid Form Quercetin Degradation in Ambient Temperature Storage The MS spectrum of the peak with a retention time 5.35 min, (relative retention 0.44) of Example 4 is shown in FIG. 7. The peak with a molecular ion mass m/z=169 and cluster of peaks with an unknown compound, that is formed under ionization with m/z=(169+98)=267, were obtained using the Q3 mode.

Figure 8:
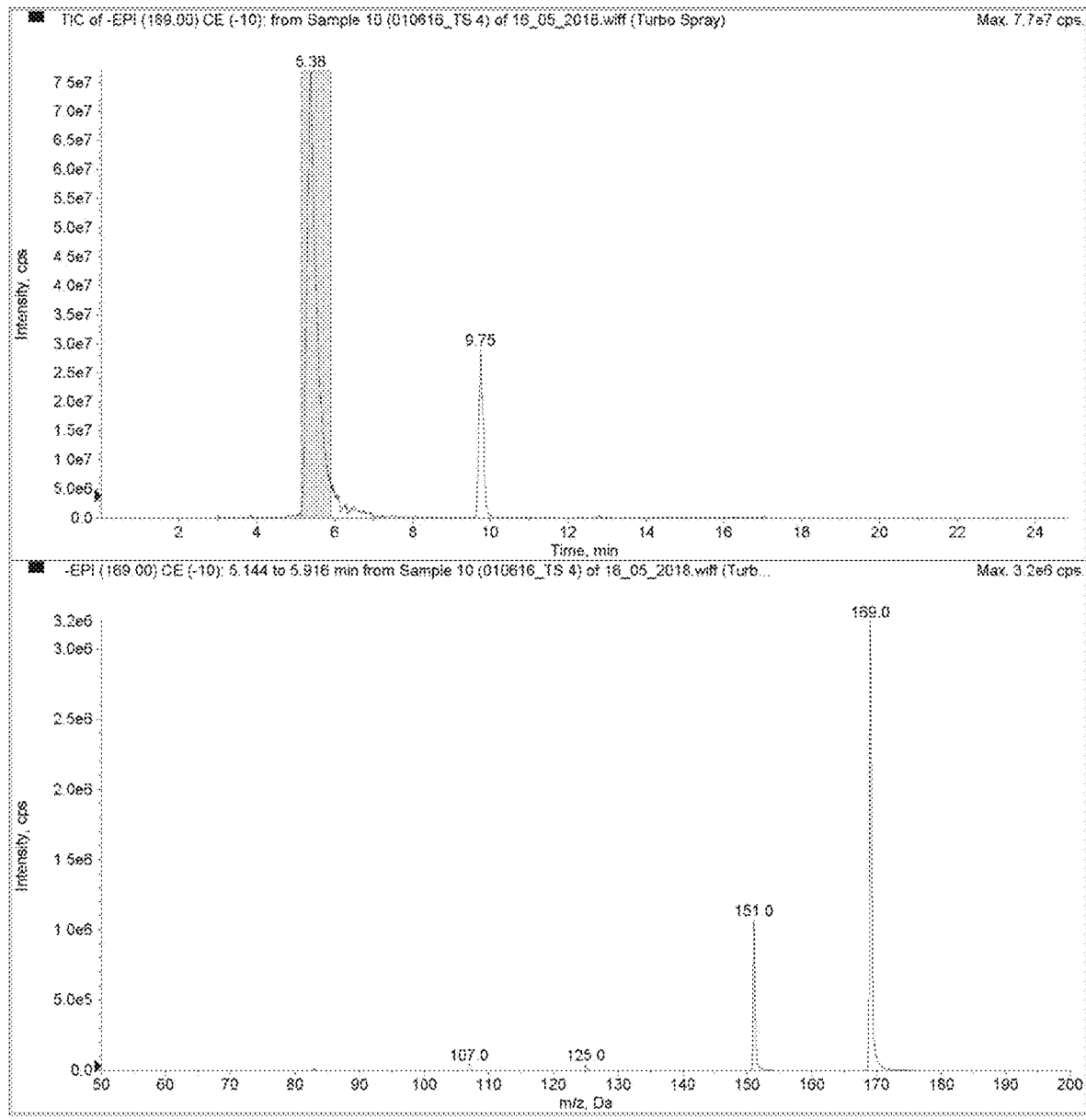
FIG. 8 shows HPLC-Mass Spectrometry results (LC (upper trace) and mass spectrum (lower trace)) of fragmentation of the molecular ion m/z=169 using EPI mode, negative polarity, collision energy −10 V.

The fragmentation of the molecular ion m/z=169 was investigated using EPI mode, negative polarity, collision energy −10 V (FIG. 8).

Figure 9:
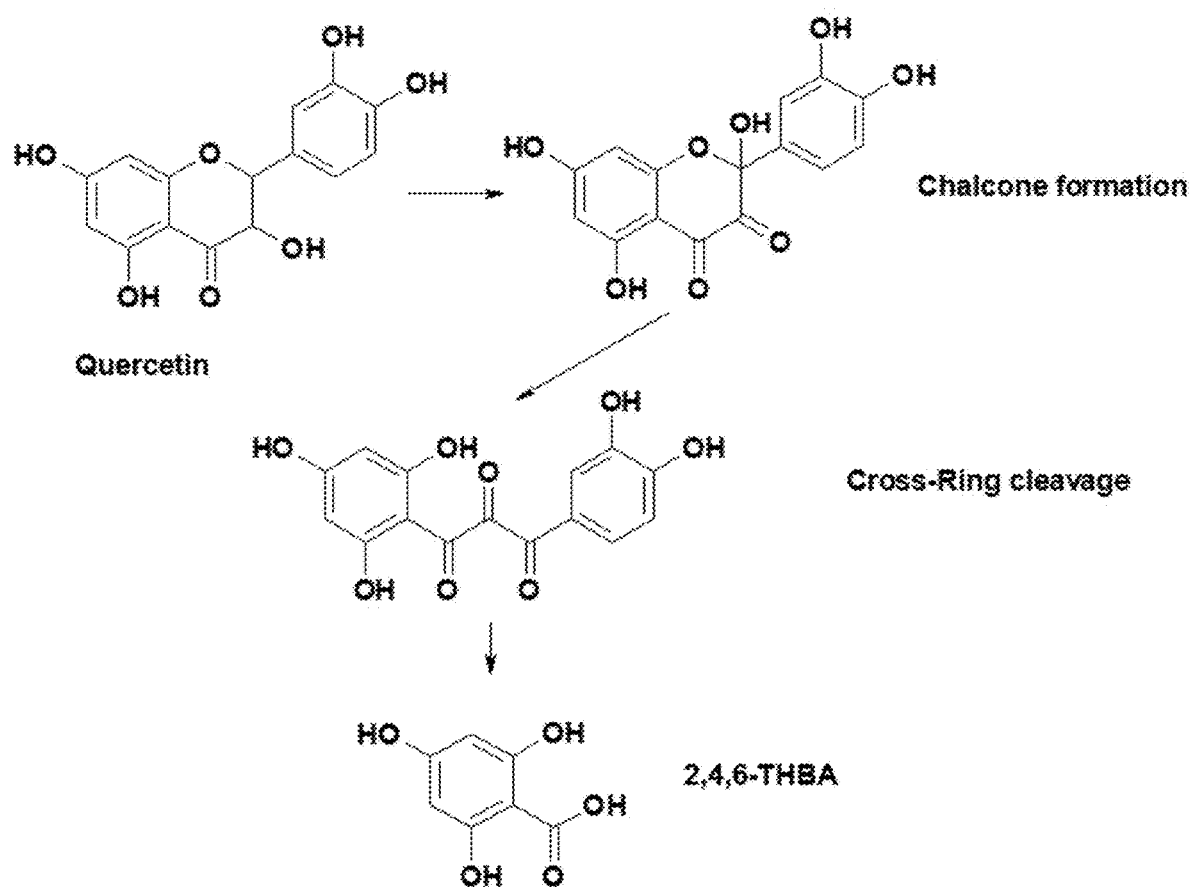
FIG. 9 shows a schema for the mechanism of formation of 2,4,6-trihydroxybenzoic acid from quercetin.

The MS spectra of fragmentation shows that the peak with a relative retention time 0.44 corresponds to 2,4,6-trihydroxybenzoic acid (2,4,6-THBA in FIG. 2). This compound is a product of quercetin degradation through the formation of an intermediate product—chalcon. The proposed chemical mechanism of formation of 2,4,6-trihydroxybenzoic acid is shown in FIG. 9.

FIG. 10 shows retention times, UV spectra and structures of 2,4,6-trihydroxybenzoic acid and quercetin. 2,4,6-trihydroxybenzoic acid has a relative retention time (RRT) 0.34, whereas RRT for quercetin is 1.0. Major absorption peaks of 2,4,6-THBA are 217, 257, and 293.5 nm while those of quercetin are 203.7, 255.6 and 366 nm.

Figure 11:
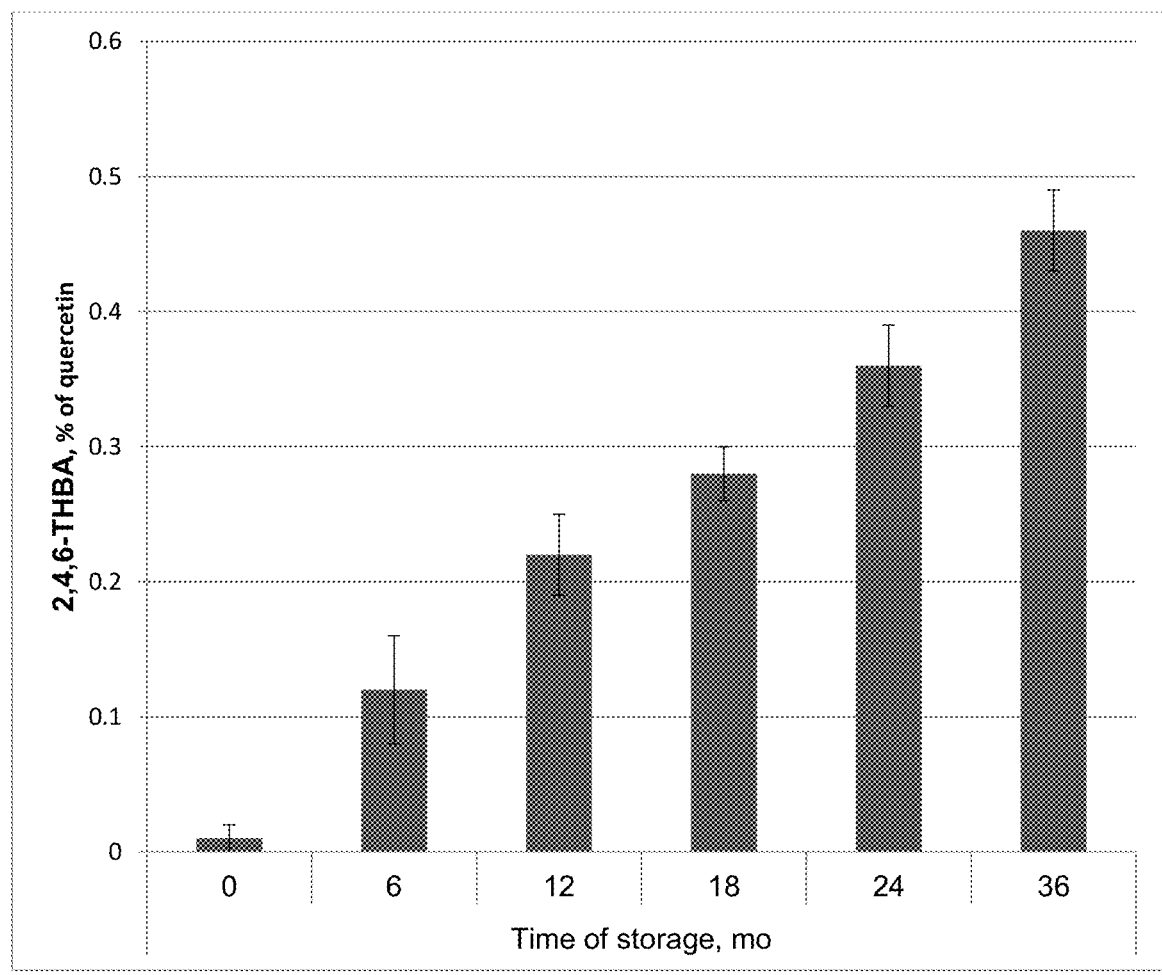
FIG. 11 shows time-dependent accumulation of 2,4,6-trihydroxybenzoic acid of solid form quercetin composition in air atmosphere under ambient temperature conditions.

FIG. 11 shows the concomitant time-dependent accumulation of 2,4,6-THBA during quercetin degradation, increasing at each time point measured, from about 0.1% (w/w) 2,4,6-trihydroxybenzoic acid/quercetin at 6 months storage to about 0.5% 2,4,6-trihydroxybenzoic acid/quercetin at 36 months storage at 20-25° C.

Data from 3 independent experiments are shown. During storage at room temperature, 2,4,6-THBA accumulated at an approximate rate of 0.15% of quercetin (w/w) per 12 months (FIG. 11).

Example 7

Figure 12:
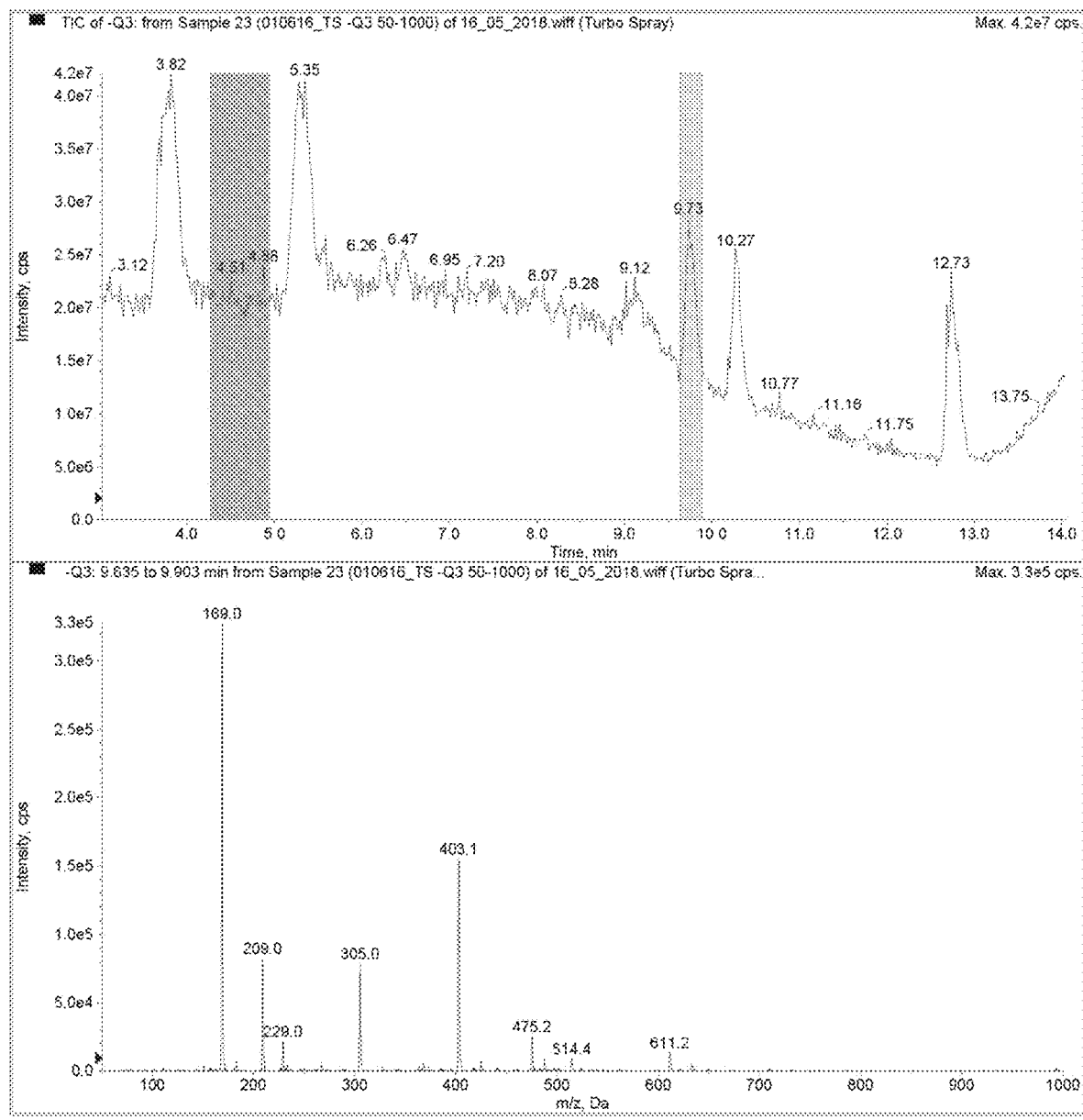
FIG. 12 shows HPLC-Mass Spectrometry results (LC (upper trace) and mass spectrum (lower trace)) of solid form quercetin stored for 18 months at 20-25° C. having a peak with a retention time 9.73 min, (relative retention 0.44) showing identification of 2-(3,4-dihydroxybenzoyloxy)-4,6-dihydroxybenzoic acid by mass spectrometry.
Figure 13:
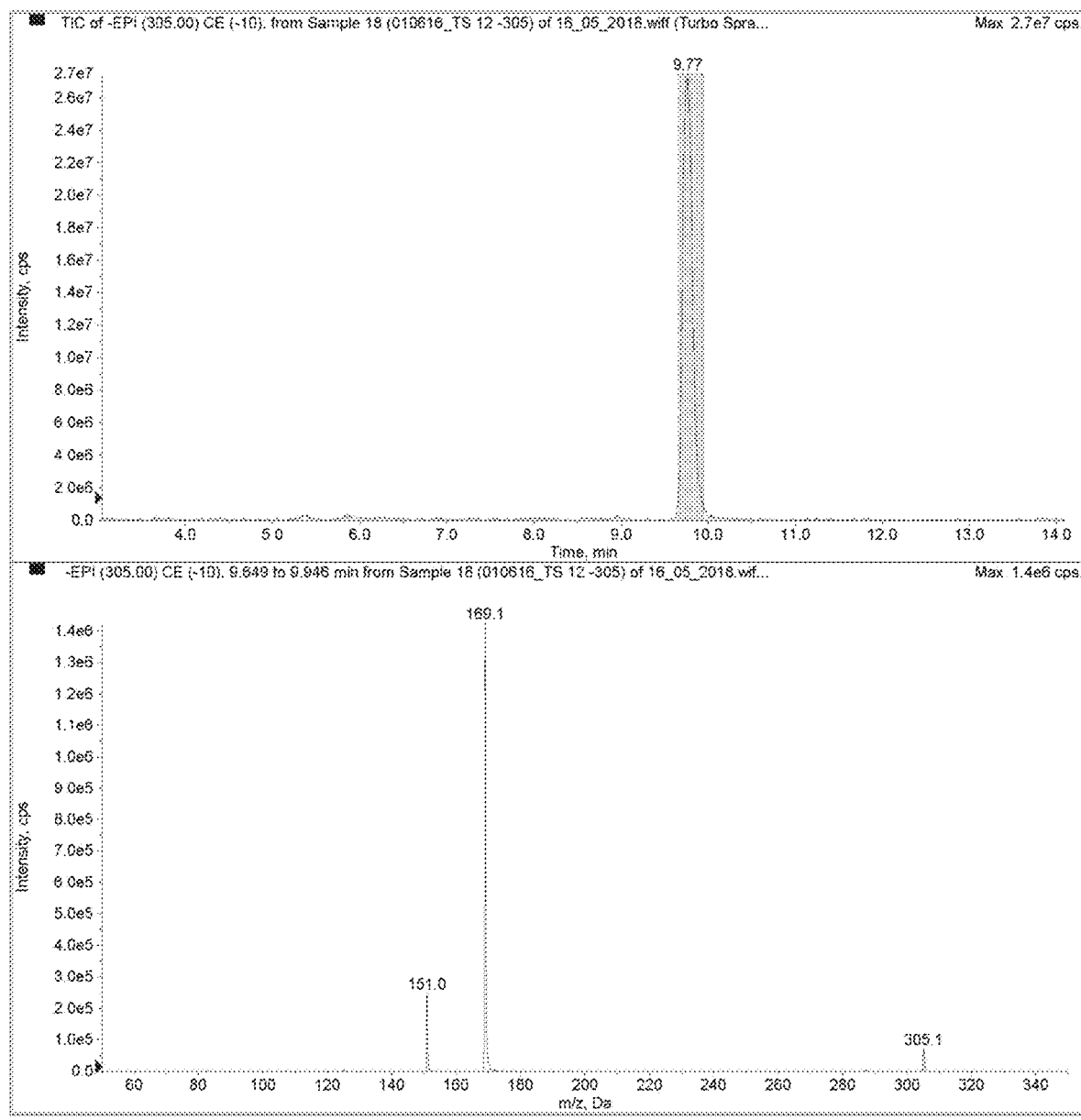
FIG. 13 shows HPLC-Mass Spectrometry results (LC (upper trace) and mass spectrum (lower trace)) of fragmentation of the molecular ion m/z=305 using EPI mode, negative polarity, collision energy −10 V.
Figure 14:
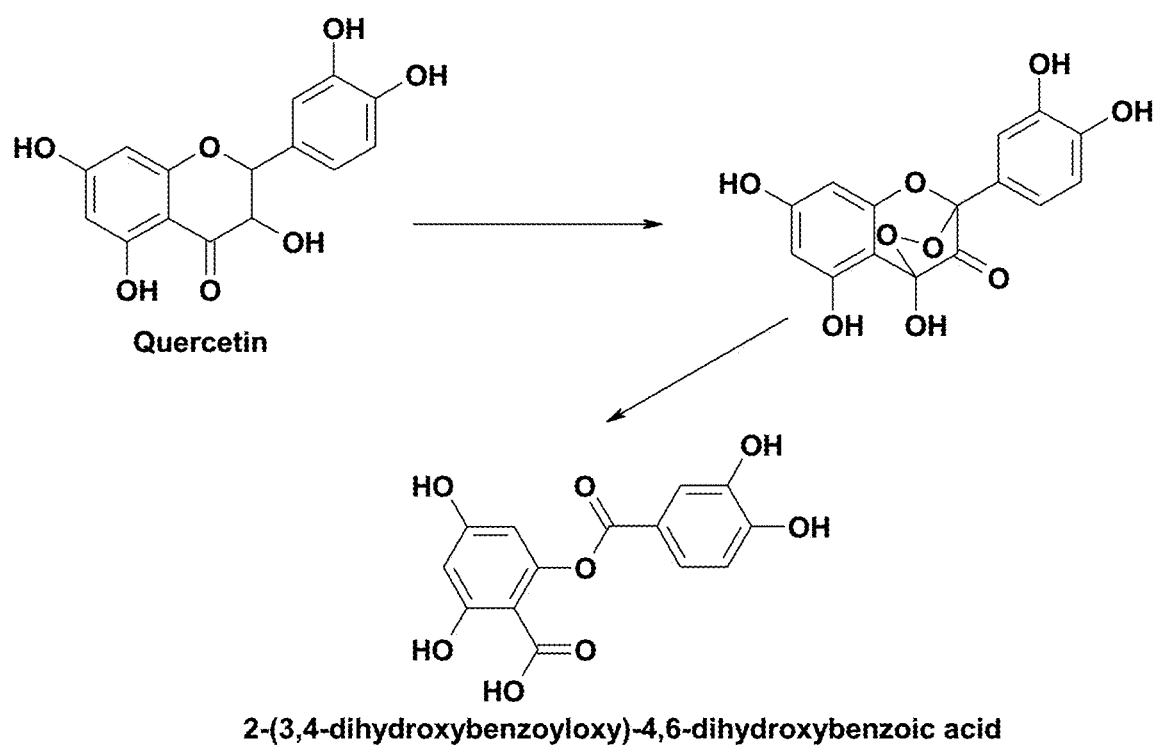
FIG. 14 shows a schema for the mechanism of formation of 2-(3,4-dihydroxybenzoyloxy)-4,6-dihydroxybenzoic acid from quercetin.

Identification of 2-[3,4-dihydrobenzol)oxy]-4,6-Dihydrobenzoic Acid as Byproduct of Solid Form Quercetin Degradation in Ambient Temperature Storage The MS spectrum of the peak with a retention time 9.73 min (relative retention 0.77) of Example 4 is shown in FIG. 12. When electrospray ionization with a negative polarity is used, the molecular ion [M-H]— m/z=305 is formed and a peak [2M-H]—m/z=611 (dimer anion) is also observed. Also observed in the mass spectrum is a cluster of peaks of an unknown compound formed under ionization conditions with m/z=(305+98)=403. The fragmentation of the molecular ion m/z=305 was investigated using EPI mode, negative polarity, with a collision energy −10 V (FIG. 13). The fragmentation shows that the peak with a relative retention 0.77 corresponds to 2-[3,4-dihydrobenzol)oxy]-4,6-dihydrobenzoic acid (DB-DBA) (FIG. 2). This compound is a product of quercetin degradation through the formation of intermediate compound cyclic peroxide quercetin. FIG. 14 shows the proposed chemical mechanism of formation of 2-(3,4-dihydroxybenzoyloxy)-4,6-dihydroxybenzoic acid during quercetin degradation.

FIG. 15 shows retention times, UV spectra and structures of DB-DBA and quercetin. DB-DBA has a relative retention time (RRT) 0.77, whereas the RRT for quercetin is 1.0. Major absorption peaks of DB-DBA are 207.9, 261.2, and 299.3 nm while those of quercetin are 203.7, 255.6 and 366 nm.

Figure 16:
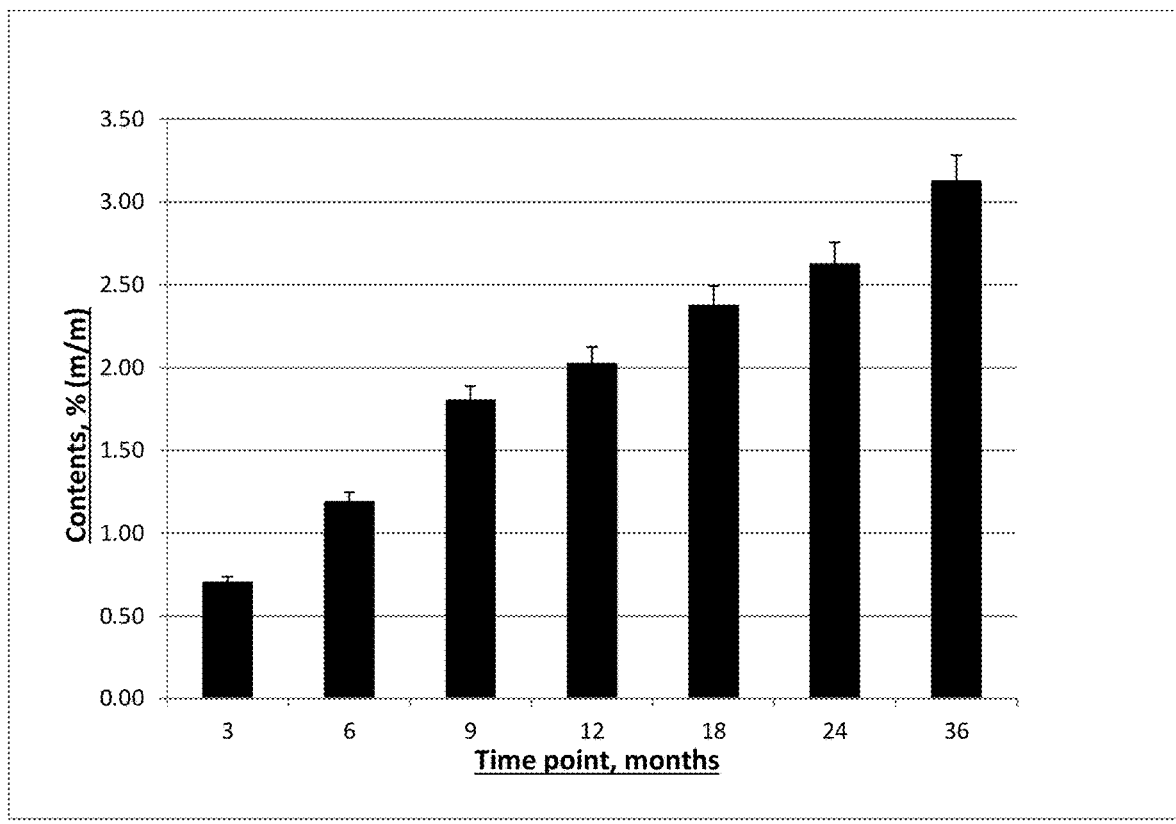
FIG. 16 shows time-dependent accumulation of 2-(3,4-dihydroxybenzoyloxy)-4,6-dihydroxybenzoic acid of solid form quercetin composition in air atmosphere under ambient temperature conditions.

Data from 3 independent experiments are shown. During storage at room temperature, DB-DBA accumulated with approximate rate of 1.25% of quercetin (w/w) per 12 months (FIG. 16).

Example 8

Determination of Safety of Quercetin Composition Based on Cytotoxicity of Protocatechuic Acid in LNCaP Human Cell Line Model A cell cytotoxicity assay is performed in 96-well plate as described (Yin et al., 2009). A sample of solid form quercetin (10%)/PVP (90%) composition containing protocatechuic acid is resuspended and introduced at increasing dilutions to the wells of a 96-well plate containing LNCaP cells ($10^5$ cells/ml) for 48 h MTT assays are performed to determine cell viability. Test cells are incubated with 0.25 mg MTT/mL for 3 h at 37 C and the amount of MTT formazan product is determined by measuring absorbance at 570 nm (630 nm as a reference) using a UV/Vis microplate reader (Bio-Rad, Hercules, Calif.). Based on absorbance curves, EC50 value are calculated. As a reference, a solution of protocatechuic acid in buffer is used as a standard.

Example 9

Determination of Safety of Quercetin Composition Based on Cytotoxicity of 2,4,6-Trihydroxybenzoic Acid in *Daphnia magna* Mobility Assay Toxicity is determined using a *Daphnia magna* mobility assay as described (Kamaya et al., 2005). Neonates (<24 h old) from 2-3-week-old mothers are placed in a 50 ml glass beaker containing 40 ml of a test solution. A sample of solid form quercetin (10%)/PVP (90%) composition containing 2,4,6-trihydroxybenzoic acid is resuspended and introduced at increasing dilutions. All experiments for exposure and controls without chemicals are made in four replicates and performed at 21±0.3° C. under 16 h light:8 h dark photoperiod. Immobility is used as the endpoint for determining acute toxicity; the daphnids showing no movement within 15 s after gentle stirring are defined to be immobile. After 24 and 48 h, the number of immobile daphnids is recorded to determine the concentration able to achieve 50% immobilization and it is indicated as EC50. The EC50 values are calculated by Probit analyses (USEPA, 1993), based on nominal concentrations and compared to similar experiments using solution of pure 2,4,6-THBA as a reference.

Example 10

Determination of Toxicity of 2-(3,4-Dihydroxybenzoyloxy)-4,6-Dihydroxybenzoic Acid Toxicity of DB-DBA (2-(3,4-dihydroxybenzoyloxy)-4,6-dihydroxybenzoic acid) was assessed in 96-well plate (Thermo Fisher, Walthman, Mass.) on $1 \times 10^3$ MDA-MB231 human breast cancer cells/well. DB-DBA was diluted in to concentrations from 500 to 0 ug/ml. The plate was incubated at 37° C. for 72 h. Cell viability was measured in a CellTiter 96® AQueous One Solution Cell Proliferation Assay (Promega, Madison, Wis.), according to the manufacturer's protocol. The absorbance at 490 nm is determined spectrophotometrically and IC50 was calculated to be 75 microgram/ml.

| DB-DBA, microgram/ml | Viability, % | SD, % |
|---|---|---|
| 0 | 100 | 0 |
| 20 | 95 | 5 |
| 50 | 62 | 7 |
| 100 | 41 | 5 |
| 250 | 19 | 3 |
| 500 | 10 | 3 |

Example 11

Figure 17:
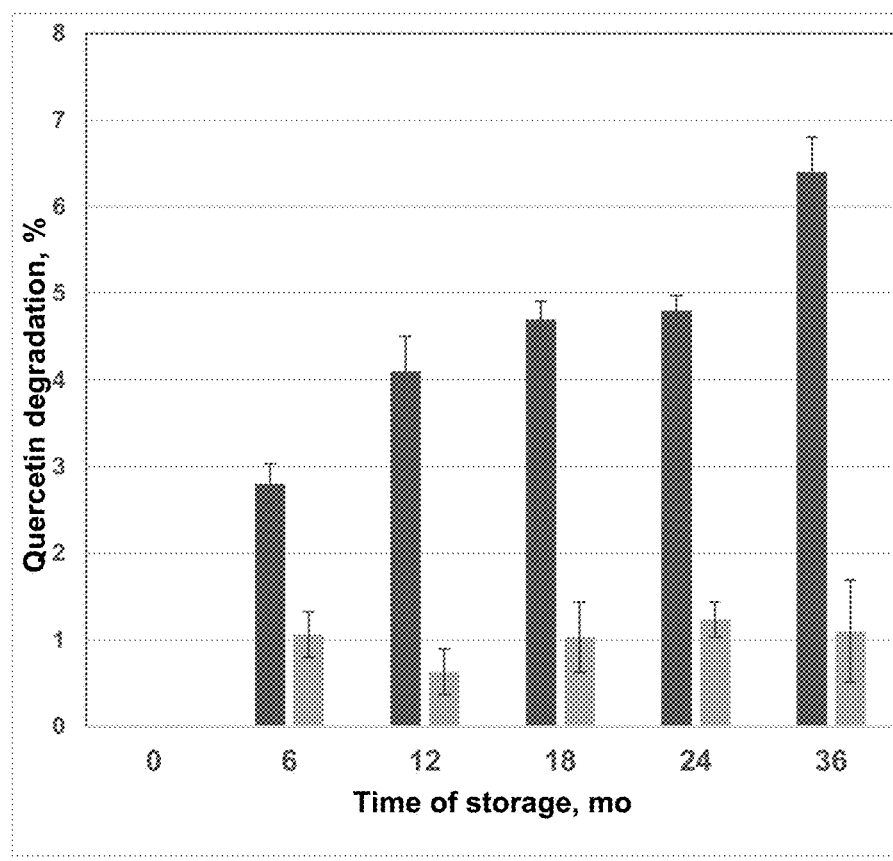
FIG. 17 shows effect of substitution of air with nitrogen gas storage atmosphere on degradation of a solid form quercetin composition.

Substitution of Air with Nitrogen Gas in Containers with Solid Form Quercetin Composition Reduces Formation of Contaminants at Ambient Temperature Vials containing (group 1) a lyophilized quercetin (10%)/PVP (90%) composition in an air atmosphere and (group 2) vials containing a lyophilized quercetin (10%)/PVP (90%) composition in a nitrogen gas atmosphere were stored at room temperature. Samples were obtained for each group at the indicated time points (0, 6, 12, 18, 24 and 36 months). Quercetin was assayed spectrophotometrically at 374 nm. The amount of quercetin remaining was calculated as average mass per vial as described above (EXAMPLE 2, FIG. 1) and the percent degradation was calculated for each. Vials containing a lyophilized quercetin (10%)/PVP (90%) composition in an air atmosphere (black columns) showed a significantly greater rate of degradation of quercetin than vials containing a lyophilized quercetin (10%)/PVP (90%) composition in a nitrogen gas atmosphere (grey columns) (FIG. 17). Degradation of quercetin was reduced by approximately 80% when the lyophilized quercetin (10%)/PVP (90%) composition was stored in a nitrogen gas atmosphere compared to an air atmosphere at the same ambient storage temperature.

Example 12

Substitution of Air with Nitrogen Gas in Containers with Solid Form Quercetin Composition Reduces Formation of Protocatechuic Acid at Ambient Temperature Vials containing (group 1) a lyophilized quercetin (10%)/PVP (90%) composition in an air atmosphere and (group 2) vials containing a lyophilized quercetin (10%)/PVP (90%) composition in a nitrogen gas atmosphere were stored at room temperature. Samples were obtained for each group at the indicated time points (0, 3, 6, 9, 12, 18, 24, and 36 months) and assayed for content of protocatechuic acid by chromatography as described above. Data from 3 independent experiments are shown. Substitution of air with nitrogen reduced accumulation of protocatechuic acid by approximately 80% (FIG. 18).

Example 13

Figure 19:
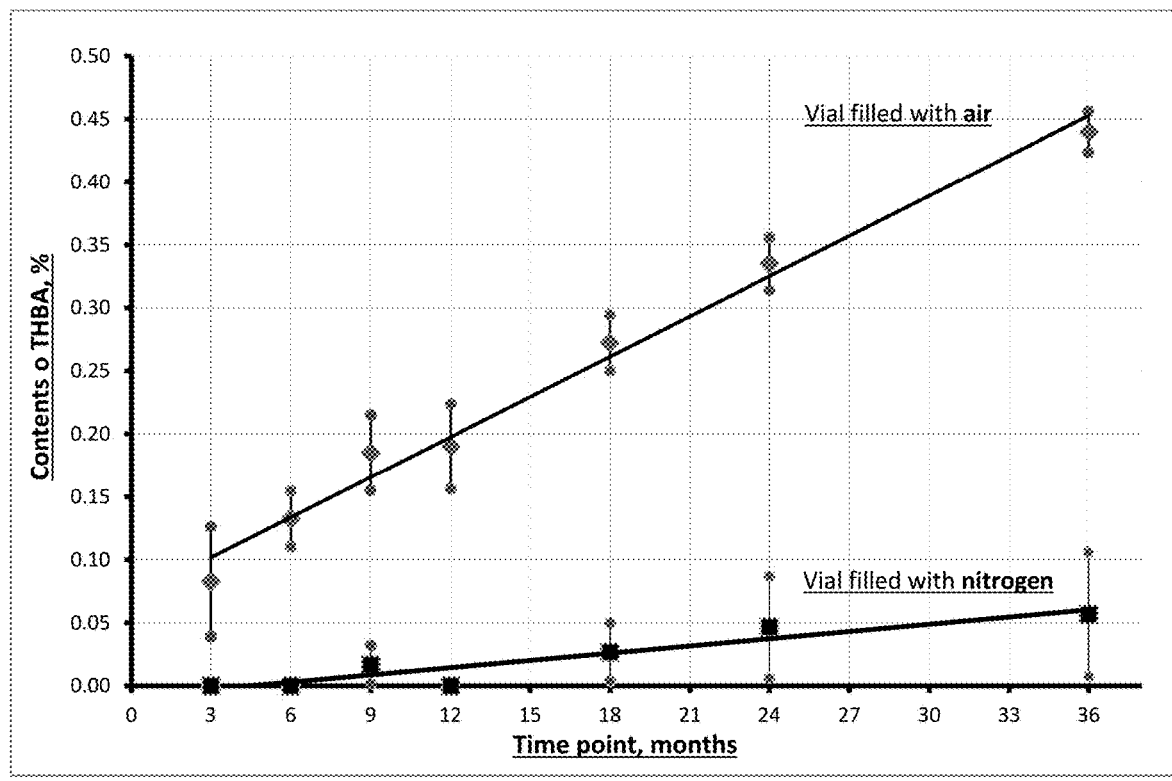
FIG. 19 shows effect of substitution of air with nitrogen gas storage atmosphere on formation of 2,4,6-THBA at ambient temperature; and, FIG. 20 shows effect of substitution of air with nitrogen gas storage atmosphere on formation of 2-(3,4-dihydroxybenzoyloxy)-4,6-dihydroxybenzoic acid at ambient temperature.

Substitution of Air with Nitrogen Gas in Containers with Solid Form Quercetin Composition Reduces Formation of 2,4,6-THBA at Ambient Temperature Vials containing (group 1) a lyophilized quercetin (10%)/PVP (90%) composition in an air atmosphere and (group 2) vials containing a lyophilized quercetin (10%)/PVP (90%) composition in a nitrogen gas atmosphere were stored at room temperature. Samples were obtained for each group at the indicated time points (0, 3, 6, 9, 12, 18, 24 and 36 months) and assayed for content of 2,4,6-THBA by chromatography as described above. Data from 3 independent experiments are shown. Substitution of air with nitrogen reduced 2,4,6-THBA accumulation by approximately 80% (FIG. 19).

Example 14

Figure 20:
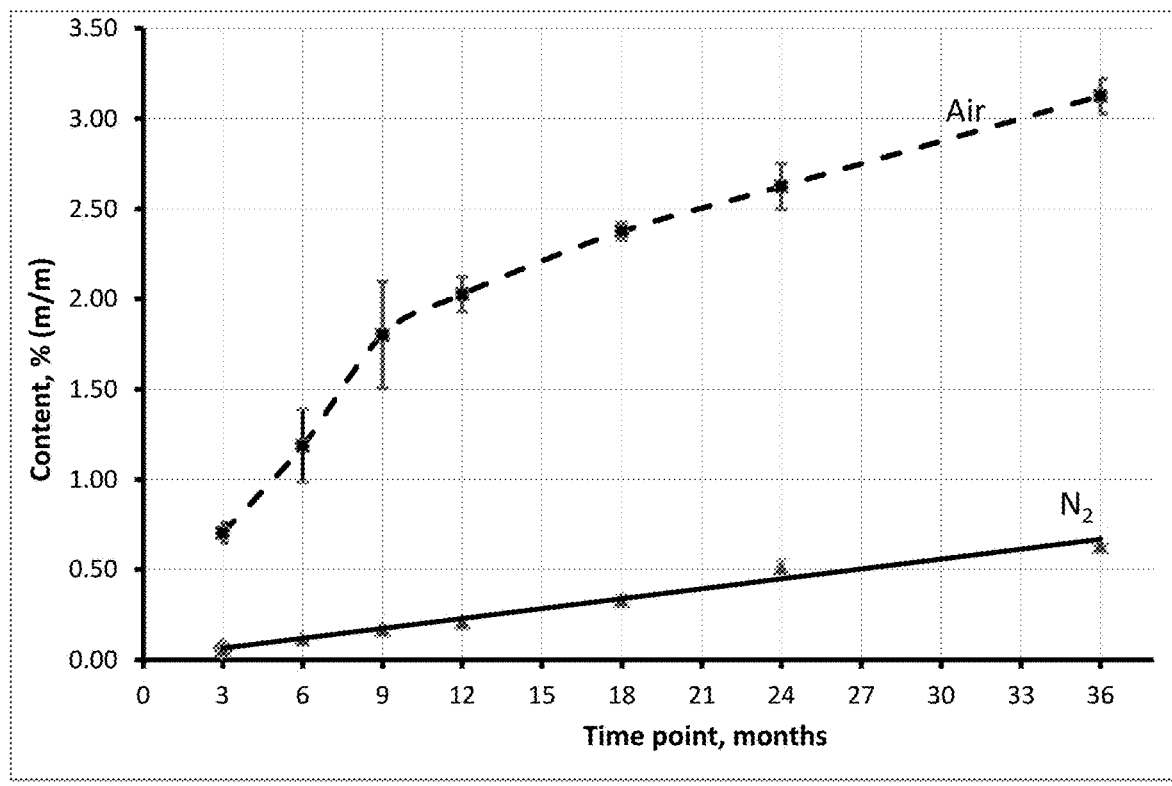

Substitution of Air with Nitrogen Gas in Containers with Solid Form Quercetin Composition Reduces Formation of 2-(3,4-Dihydroxybenzoyloxy)-4,6-Dihydroxybenzoic Acid at Ambient Temperature Vials containing a lyophilized quercetin (10%)/PVP (90%) composition in an air atmosphere and vials containing a lyophilized quercetin (10%)/PVP (90%) composition in a nitrogen gas atmosphere were stored at room temperature. Samples were obtained for each group at the indicated time points (0, 3, 6, 9, 12, 18, 24 and 36 months) and assayed for content of 2-(3,4-dihydroxybenzoyloxy)-4,6-dihydroxybenzoic acid by chromatography as described above. Data from 3 independent experiments are shown. Substitution of air with nitrogen reduced DB-DBA accumulation by approximately 80% (FIG. 20)

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

The above disclosure is intended only to convey an understanding of the present invention to those skilled in the art, and is not intended to be limiting. It will be appreciated that various modifications to the disclosed embodiments are possible without departing from the scope of the invention. Therefore, the scope of the present invention should be construed solely by reference to the appended claims.

What is claimed is:

1. A method of assessing safety of a quercetin composition comprising:
    determining a level of a contaminant in the quercetin composition, wherein the contaminant is selected from the group consisting of: protocatechuic acid, 2,4,6-trihydroxybenzoic acid, and 2-(3,4-dihydroxybenzoyloxy)-4,6-dihydroxybenzoic acid
    comparing the level of contaminant to a threshold level;
    wherein the quercetin composition is identified as unsafe if the level of contaminant is above the threshold level; and,
    wherein the quercetin composition is identified as not unsafe if the level of contaminant is below the threshold level.

2. The method of claim 1, wherein the contaminant is protocatechuic acid and the threshold level is about 0.6%, about 0.5%, about 0.4%, about 0.3%, or about 0.2% (w/w) of protocatechuic acid/quercetin.

3. The method of claim 1, wherein the contaminant is protocatechuic acid and the threshold level is about 0.12±0.02% (w/w) of protocatechuic acid/quercetin.

4. The method of claim 1, wherein the contaminant is 2,4,6-trihydroxybenzoic acid and the threshold level of 2,4,6-trihydroxybenzoic acid is about 0.17%, about 0.16%, about 0.15%, about 0.14%, about 0.13%, about 0.12%, about 0.11%, about 0.10%, about 0.09%, or about 0.08% (w/w) 2,4,6-THBA/quercetin.

5. The method of claim 1, wherein the contaminant is 2,4,6-trihydroxybenzoic acid and the threshold level of 2,4,6-trihydroxybenzoic acid is about 0.05±0.02% (w/w) of 2,4,6-trihydroxybenzoic acid/quercetin.

6. The method of claim 1, wherein the contaminant is 2-(3,4-dihydroxybenzoyloxy)-4,6-dihydroxybenzoic acid and the threshold level of 2-(3,4-dihydroxybenzoyloxy)-4,6-dihydroxybenzoic acid is about 2%, about 1.5%, about 1%, about 0.9%, about 0.8%, about 0.7% or about 0.6% (w/w) of 2-(3,4-dihydroxybenzoyloxy)-4,6-dihydroxybenzoic acid/quercetin.

7. The method of claim 1, wherein the contaminant is 2-(3,4-dihydroxybenzoyloxy)-4,6-dihydroxybenzoic acid and the threshold level of 2-(3,4-dihydroxybenzoyloxy)-4,6-dihydroxybenzoic acid is about 0.51±0.03% (w/w) of 2-(3,4-dihydroxybenzoyloxy)-4,6-dihydroxybenzoic acid/quercetin.

8. A method of assessing safety of a quercetin composition comprising:
    determining a level of at least two contaminants in the quercetin composition, wherein the contaminants are selected from the group consisting of: protocatechuic acid, 2,4,6-trihydroxybenzoic acid, and 2-(3,4-dihydroxybenzoyloxy)-4,6-dihydroxybenzoic acid comparing the level of the at least two contaminants in combination to a threshold level;
    wherein the quercetin composition is identified as unsafe if the level of the at least two contaminants in combination is above the threshold level; and,
    wherein the quercetin composition is identified as not unsafe if the level of the at least two contaminants in combination is below the threshold level.

9. The method of claim 8, wherein the threshold level is 1 and calculated for the contaminants determined by the equation: (% (w/w) of protocatechuic acid/quercetin)/T1+(% (w/w) of 2,4,6-trihydroxybenzoic acid/quercetin)/T2+(% (w/w) of 2-(3,4-dihydroxybenzoyloxy)-4,6-dihydroxybenzoic acid/quercetin)/T3;
    wherein T1 is the threshold level of protocatechuic acid, T2 is the threshold level of 2,4,6-trihydroxybenzoic acid, and T3 is the threshold level of 2-(3,4-dihydroxybenzoyloxy)-4,6-dihydroxybenzoic acid/quercetin; and,
    wherein for a contaminant not selected to be determined, the contribution to the threshold level is zero.

10. The method of claim 8, wherein the threshold level is 1 and calculated for the contaminants determined by the equation: (% (w/w) of protocatechuic acid/quercetin)/0.65+(% (w/w) of 2,4,6-trihydroxybenzoic acid/quercetin)/0.33+(% (w/w) of 2-(3,4-dihydroxybenzoyloxy)-4,6-dihydroxybenzoic acid/quercetin)/2.6;
    wherein for a contaminant not selected to be determined, the contribution to the threshold level is zero.

11. The method of claim 1, wherein the quercetin composition further comprises a drug delivery formulation.

12. The method of claim 11, wherein the drug delivery formulation is selected from the group consisting of: a lipid-based carrier, a polymer-based carrier, nanoparticles, inclusion complexes, micelles, and a conjugate-based capsulation.

13. The method of claim 12, wherein the drug delivery formulation comprises a lipid-based carrier and the lipid-based carrier is selected from the group consisting of: glycerin, propylene glycol, stearate, and olive oil.

14. The method of claim 12, wherein the quercetin composition comprises 7-11% quercetin and 89-93% polyvinylpyrrolidone w/w.

15. The method of claim 1, wherein determining the level of a contaminant in the quercetin composition comprises chromatography.

16. The method of claim 15, wherein the chromatography is selected from the group consisting of: liquid chromatography, thin layer chromatography, gas chromatography, and electrophoresis.

17. The method of claim 16, wherein liquid chromatography comprises high-performance (HPLC) or ultra performance (UPLC) liquid chromatography.

18. The method of claim 15, further comprising ultraviolet, diode-array, mass, evaporating light scattering, conductometric, electrochemical, or fluorescence detection.

19. The method of claim 16, wherein the chromatography is gas chromatography and further comprises flame-ionizing or mass detection.

* * * * *